United States Patent
Wang et al.

(10) Patent No.: US 12,191,891 B2
(45) Date of Patent: Jan. 7, 2025

(54) SYSTEMS AND METHODS FOR DATA STORAGE

(71) Applicant: WUHAN UNITED IMAGING HEALTHCARE CO., LTD., Hubei (CN)

(72) Inventors: Dingxin Wang, Wuhan (CN); Yaguang Wang, Wuhan (CN); Chao Xia, Wuhan (CN); Xing Ming, Wuhan (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 316 days.

(21) Appl. No.: 17/452,778

(22) Filed: Oct. 29, 2021

(65) Prior Publication Data
US 2022/0140840 A1 May 5, 2022

(30) Foreign Application Priority Data

Oct. 29, 2020 (CN) .......................... 202011185170.3
Nov. 5, 2020 (CN) .......................... 202011222321.8
(Continued)

(51) Int. Cl.
*G06F 16/51* (2019.01)
*G16H 30/20* (2018.01)
(Continued)

(52) U.S. Cl.
CPC .......... *H03M 7/3064* (2013.01); *G06F 16/51* (2019.01); *G16H 30/20* (2018.01); *G16H 30/40* (2018.01)

(58) Field of Classification Search
CPC ....... G06F 16/51; G06F 16/538; G06F 16/532
See application file for complete search history.

(56) References Cited

U.S. PATENT DOCUMENTS 5,828,814 A  10/1998 Cyman et al.
6,246,804 B1 *  6/2001 Sato ...................... G06F 16/532
                                                     382/284
(Continued)

FOREIGN PATENT DOCUMENTS

CN  102129474 A  7/2011
CN  106202848 A  12/2016
(Continued)

OTHER PUBLICATIONS

Koohbanani et al., "NuClick: A Deep Learning Framework for Interactive Segmentation of Microscopy Images", Jul. 2020 arXiv:2005.14511v2 [cs.CV] (Year: 2020).*
(Continued)

*Primary Examiner* — Hosain T Alam
*Assistant Examiner* — Robert F May
(74) *Attorney, Agent, or Firm* — METIS IP LLC

(57) ABSTRACT

A method for data storage may be provided. The method may include storing metadata of an image file onto a first storage device. The method may include dividing image data of the image file into at least one sub-image data set. The method may also include storing each sub-image data set of the at least one sub-image data set, onto a second storage device of at least one second storage device. The method may further include storing access information of the at least one second storage device onto the first storage device.

17 Claims, 23 Drawing Sheets

(30) Foreign Application Priority Data

Dec. 10, 2020 (CN) .......................... 202011435223.2
Dec. 23, 2020 (CN) .......................... 202011541653.2

(51) Int. Cl.
*G16H 30/40* (2018.01)
*H03M 7/30* (2006.01)

(56) References Cited

U.S. PATENT DOCUMENTS

| | | | |
|---|---|---|---|
| 6,954,802 | B2 | 10/2005 | Sutherland et al. |
| 9,235,889 | B1 | 1/2016 | Frenkel et al. |
| 9,465,858 | B2 | 10/2016 | Pennefather et al. |
| 10,257,174 | B2 | 4/2019 | Rosenberg et al. |
| 2001/0019587 | A1 | 9/2001 | Hashimoto et al. |
| 2001/0051881 | A1 | 12/2001 | Filler |
| 2006/0206547 | A1 | 9/2006 | Kulkarni et al. |
| 2006/0256380 | A1* | 11/2006 | Klassen ................. H04N 19/12 375/E7.137 |
| 2007/0064981 | A1* | 3/2007 | Meijer ................... G06T 7/0012 382/128 |
| 2007/0076961 | A1* | 4/2007 | Shiiyama ............... H04N 19/46 382/232 |
| 2010/0021001 | A1* | 1/2010 | Honsinger ............. G06T 1/0028 713/168 |
| 2011/0282844 | A1 | 11/2011 | Bates et al. |
| 2012/0209833 | A1* | 8/2012 | Kramer .................. G06F 16/58 707/723 |
| 2014/0254934 | A1* | 9/2014 | Laxminarayana Bhat .................. G06F 16/58 382/173 |
| 2016/0125135 | A1 | 5/2016 | Ramanathan et al. |
| 2017/0206331 | A1 | 7/2017 | Veliah et al. |
| 2019/0095478 | A1* | 3/2019 | Tankersley .......... G06F 11/3006 |
| 2020/0076578 | A1* | 3/2020 | Ithal .................... H04L 63/0272 |
| 2020/0273559 | A1 | 8/2020 | Yousfi et al. |
| 2020/0372031 | A1 | 11/2020 | Ruehle |
| 2020/0411164 | A1* | 12/2020 | Donner ................. G16H 30/20 |
| 2021/0287329 | A1* | 9/2021 | Thakkar .................... G06T 1/60 |
| 2024/0086460 | A1* | 3/2024 | Ben Shaul ............ G06F 16/538 |

FOREIGN PATENT DOCUMENTS

| | | | |
|---|---|---|---|
| CN | 106850758 | A | 6/2017 |
| CN | 106909780 | A * | 6/2017 |
| CN | 107180199 | A | 9/2017 |
| CN | 107704604 | A | 2/2018 |
| CN | 109411056 | A | 3/2019 |
| CN | 109584233 | A | 4/2019 |
| CN | 109684331 | A | 4/2019 |
| CN | 109710614 | A | 5/2019 |
| CN | 109740366 | A | 5/2019 |
| CN | 110110550 | A | 8/2019 |
| CN | 110535624 | A | 12/2019 |
| CN | 110570928 | A * | 12/2019 |
| CN | 110729034 | A | 1/2020 |
| CN | 110825698 | A | 2/2020 |
| CN | 110990877 | A | 4/2020 |
| CN | 111225375 | A | 6/2020 |
| CN | 111739613 | A | 10/2020 |
| JP | 4620165 | B2 | 1/2011 |
| JP | 2019079355 | A | 5/2019 |

OTHER PUBLICATIONS

Maninis et al., "Deep Extreme Cut: From Extreme Points to Object Segmentation", Mar. 2018, arXiv:1711.09081v2 [cs.CV] (Year: 2018).*

Sakinis et al., "Interactive segmentation of medical images through fully convolutional neural networks", Mar. 2019, arXiv:1903.08205v1 [cs.CV] (Year: 2019).*

Benenson et al., "Large-scale interactive object segmentation with human annotators", Apr. 2019, arXiv:1903.10830v2 [cs.CV] (Year: 2019).*

Wang et al., "Interactive Medical Image Segmentation Using Deep Learning With Image-Specific Fine Tuning", Jul. 2018, IEEE Transactions on Medical Imaging, vol. 37, No. 7 (Year: 2018).*

Liu et al., "Machine Vision Guided 3D Medical Image Compression for Efficient Transmission and Accurate Segmentation in the Clouds", Apr. 2019, arXiv:1904.08487v1 [cs.CV] (Year: 2019).*

First Office Action in Chinese Application No. 202011185170.3 mailed on Jan. 20, 2022, 8 pages.

First Office Action in Chinese Application No. 202011222321.8 mailed on Jan. 21, 2022, 10 pages.

First Office Action in Chinese Application No. 202011435223.2 mailed on Apr. 1, 2022, 11 pages.

First Office Action in Chinese Application No. 202011541653.2 mailed on Jan. 24, 2022, 9 pages.

The Extended European Search Report in European Application No. 21205586.7 mailed on Mar. 21, 2022, 12 pages.

The Extended European Search Report in European Application No. 21205635.2 mailed on Mar. 23, 2022, 12 pages.

Medical Imaging & Technology Alliance: DICOM PS3.1 2019e—Part 1: Introduction and Overview, 2019, 34 pages.

Medical Imaging & Technology Alliance: DICOM PS3.4 2019e—Part 4: Service Class Specifications, 2019, 400 pages.

Medical Imaging & Technology Alliance: DICOM PS3.5 2019e—Part 5: Data Structures and Encoding, 2019, 150 pages.

Medical Imaging & Technology Alliance: DICOM PS3.6 2019e—Part 6: Data Dictionary, 2019, 248 pages.

Medical Imaging & Technology Alliance: DICOM PS3.7 2019e—Part 7: Message Exchange, 2019, 128 pages.

Medical Imaging & Technology Alliance: DICOM PS3.10 2019e—Part 10: Media Storage and File Format for Media Interchange, 2019, 50 pages.

* cited by examiner

SYSTEMS AND METHODS FOR DATA STORAGE

CROSS-REFERENCE TO RELATED APPLICATIONS

This application claims priority to Chinese Application No. 202011185170.3 filed on Oct. 29, 2020, Chinese Patent Application No. 202011222321.8, filed on Nov. 5, 2020, Chinese Application No. 202011435223.2 filed Dec. 10, 2020, and Chinese Application No. 202011541653.2 filed on Dec. 23, 2020, the contents of each of which are hereby incorporated by reference.

TECHNICAL FIELD

The present disclosure relates to file management, and in particular, to systems and methods for file transmission and archiving.

BACKGROUND

With the development of cloud computing, more and more industries (e.g., a medical industry) store data using cloud storage. Conventionally, data to be stored needs to be uploaded to a cloud server for storage. When a user needs to obtain the stored data, the user directly downloads the data from the cloud server. However, medical data usually contains a large amount of image data, so its storage efficiency and query speed are low. It is desirable to provide efficient systems and methods for medical data storage.

SUMMARY

According to an aspect of the present disclosure, a system for data storage may be provided. The system may include at least one storage device and at least one processor configured to communicate with the at least one storage device. The at least one storage device may include a set of instructions. When the at least one processor execute the set of instructions, the at least one processor may be directed to cause the system to perform one or more of the following operations. The system may store metadata of an image file onto a first storage device. The system may divide image data of the image file into at least one sub-image data set. The system may also store each sub-image data set of the at least one sub-image data set onto a second storage device of at least one second storage device. The system may further store access information of the at least one second storage device onto the first storage device.

In some embodiments, to store the metadata of the image file onto the first storage device, the system may obtain encrypted metadata by encrypting the metadata of the image file. The system may further store the encrypted metadata onto the first storage device.

In some embodiments, to divide the image data of the image file into at least one sub-image data set, the system may obtain compressed image data by compressing the image data of the image file. The system may further divide the compressed image data into the at least one sub-image data set.

In some embodiments, the system may further perform one or more of the following operations. The system may obtain at least one encoded sub-image data set by encoding the at least one sub-image data set. To store each sub-image data set of the at least one sub-image data set onto a second storage device of the at least one second storage device, the system may store each encoded sub-image data set of the at least one encoded sub-image data set onto a second storage device of the at least one second storage device.

In some embodiments, the system may further perform one or more of the following operations. The system may obtain access information of the at least one second storage device, the system may further generate the metadata of the image file based on the access information of the image data.

In some embodiments, the image file may include a plurality of image slices. The metadata of the image file may include index information of the plurality of image slices. The system may further perform one or more of the following operations. The system may identify a series instance unique identifier (UID) of the plurality of image slices. The system may further determine index information of the plurality of image slices based on the series instance UID. The index information may include the series instance UID.

In some embodiments, the system may further perform one or more of the following operations. The system may modify or delete the at least a portion of the image file. The system may further update the metadata of the image file.

According to another aspect of the present disclosure, a system for accessing data may be provided. The system may include at least one storage device and at least one processor configured to communicate with the at least one storage device. The at least one storage device may include a set of instructions. When the at least one processor execute the set of instructions, the at least one processor may be directed to cause the system to perform one or more of the following operations. The system may obtain a request for accessing an image file from a user terminal. The system may obtain metadata of the image file based on the request from a first storage device. The system may also obtain access information of at least one second storage device that stores image data of the image file based on the metadata from the first storage device. The system may also obtain at least one sub-image data set of the image data from the at least one second storage device. The system may further obtain the image file by combining the metadata and the at least one sub-image data set.

In some embodiments, the request may further include modifying or deleting at least a portion of the image file, and the system may perform one or more of the following operations. The system may modify or delete the at least a portion of the obtained image file based on the request. The system may further update at least a portion of the metadata of the image file.

In some embodiments, the metadata of the image file may be encrypted. To obtain the metadata of the image file based on the request from the first storage device, the system may obtain decrypted metadata by decrypting the metadata obtained from the first storage device.

In some embodiments, to obtain the image file by combining the metadata and the at least one sub-image data set, the system may obtain compressed image data by combining the at least one sub-image data set. The system may also obtain decompressed image data by decompressing the compressed image data. The system may further obtain the image file by combining the decompressed image data and the decrypted metadata.

According to yet another aspect of the present disclosure, a system for archiving data may be provided. The system may include at least one storage device and at least one processor configured to communicate with the at least one storage device. The at least one storage device may include a set of instructions. When the at least one processor execute the set of instructions, the at least one processor may be directed to cause the system to perform one or more of the following operations. The system may obtain an image file. The system may store image data of the image file onto the at least one storage device. The system may obtain access information of the image data stored on the at least one storage device. The system may generate metadata of the image file based on the access information of the image data.

In some embodiments, the system may further compress the image data of the image file before storing the image data.

In some embodiments, the system may further determine a file count of image data in the at least one storage device or an occupied storage space of the at least one storage device after the image data of the image file is store onto the at least one storage device.

In some embodiments, the system may further perform one or more of the following operations. The system may modify or delete the at least a portion of the image file. The system may further update the metadata of the image file.

According to yet another aspect of the present disclosure, a system for assessing data may be provided. The system may include at least one storage device and at least one processor configured to communicate with the at least one storage device. The at least one storage device may include a set of instructions. When the at least one processor execute the set of instructions, the at least one processor may be directed to cause the system to perform one or more of the following operations. The system may obtain a request for accessing image data of an image file from a user terminal. The system may also obtain metadata of the image data based on the request. The system may further obtain the image data by accessing the at least one storage device based on the metadata.

In some embodiments, to obtain the image data by accessing the at least one storage device based on the metadata, the system may obtain a frequency count by which the metadata or the image data of the image file are accessed. The system may further determine whether the metadata or the image data is frequently accessed based on the frequency count. In response to determining that the metadata or the image data is frequently accessed, the system may obtain the image data from a buffer, wherein the buffer stores the image data. In response to determining that the metadata or the image data is not frequently accessed, the system may obtain the image data from the at least one storage device.

In some embodiments, the request may further include modifying or deleting at least a portion of the image file, and the system may further perform one or more of the following operations. The system may modify or delete the at least a portion of the obtained image data based on the request. The system may update at least a portion of the metadata of the image file.

According to yet another aspect of the present disclosure, a system for determining index information may be provided. The system may include at least one storage device and at least one processor configured to communicate with the at least one storage device. The at least one storage device may include a set of instructions. When the at least one processor execute the set of instructions, the at least one processor may be directed to cause the system to perform one or more of the following operations. The system may obtain a plurality of image slices. The system may also identify a series instance unique identifier (UID) of the plurality of image slices. The system may further determine index information of the plurality of image slices based on the series instance UID. The index information may include the series instance UID.

In some embodiments, the index information may further include a hash value of a last image of the plurality of image slices.

In some embodiments, to determine the index information of the plurality of image slices based on the series instance unique identifier UID, for each image slice of the plurality of image slices, the system may determine a hash value. A hash value of a first image slice which is immediately next to a second image slice of the plurality of image slices may be determined based on a hash value of the second image slice according to a hash algorithm.

In some embodiments, a hash value of a lead image slice of the plurality of image slices may be designated as the series instance UID.

In some embodiments, the index information may further include a storage ID of a storage device that stores the lead image slice.

In some embodiments, the plurality of image slices may be stored according to a network attached storage (NAS), and the hash value for each image slice of the plurality of image slices may be designated as an ID of the image slice.

In some embodiments, the plurality of image slices may be stored according to an object storage service (OSS), and the hash value for each image slice of the plurality of image slices may be designated as an ID of an image file of the image slice.

According to yet another aspect of the present disclosure, a system for assessing data may be provided. The system may include at least one storage device and at least one processor configured to communicate with the at least one storage device. The at least one storage device may include a set of instructions. When the at least one processor execute the set of instructions, the at least one processor may be directed to cause the system to perform one or more of the following operations. The system may obtain a series instance UID from a user terminal. The system may obtain index information based on the series instance UID. The system may also determine whether the index information includes a hash value. In response to determining that the index information does not include the hash value, the system may further obtain an image identified as the series instance UID.

According to yet another aspect of the present disclosure, a method for data storage may be provided. The method may include storing metadata of an image file onto a first storage device. The method may include dividing image data of the image file into at least one sub-image data set. The method may also include storing each sub-image data set of the at least one sub-image data set, onto a second storage device of at least one second storage device. The method may further include storing access information of the at least one second storage device onto the first storage device.

According to yet another aspect of the present disclosure, a method for assessing data may be provided. The method may include obtaining a request for accessing an image file from a user terminal. The method may include obtaining metadata of the image file based on the request from a first storage device. The method may also include obtaining access information of at least one second storage device that stores image data of the image file based on the metadata from the first storage device. The method may also include obtaining at least one sub-image data set of the image data from the at least one second storage device. The method may further include obtaining the image file by combining the metadata and the at least one sub-image data set.

According to yet another aspect of the present disclosure, a method for archiving data may be provided. The method may include obtaining an image file. The method may include storing image data of the image file onto at least one storage device. The method may also include obtaining access information of the image data stored on the at least one storage device. The method may further include generating metadata of the image file based on the access information of the image data.

According to yet another aspect of the present disclosure, a method for assessing data may be provided. The method may include obtaining a request for accessing image data of an image file from a user terminal. The method may also include obtaining metadata of the image data based on the request. The method may further include obtaining the image data by accessing at least one storage device based on the metadata.

According to yet another aspect of the present disclosure, a method for determining index information may be provided. The method may include obtaining a plurality of image slices. The method may include identifying a series instance unique identifier (UID) of the plurality of image slices. The method may include determining index information of the plurality of image slices based on the series instance UID. The index information may include the series instance UID.

According to yet another aspect of the present disclosure, a method for assessing data may be provided. The method may include obtaining a series instance UID from a user terminal. The method may include obtaining index information based on the series instance UID. The method may include also determining whether the index information includes a hash value. In response to determining that the index information does not include the hash value, the method may further include obtaining an image identified as the series instance UID.

According to yet another aspect of the present disclosure, a non-transitory computer readable medium may be provided. The non-transitory computer readable may include executable instructions for data storage. When executed by at least one processor of a computing device, the executable instructions may cause the computing device to perform a method. The method may include dividing image data of the image file into at least one sub-image data set. The method may also include storing each sub-image data set of the at least one sub-image data set, onto a second storage device of at least one second storage device. The method may further include storing access information of the at least one second storage device onto the first storage device.

According to yet another aspect of the present disclosure, a non-transitory computer readable medium may be provided. The non-transitory computer readable may include executable instructions for assessing data. When executed by at least one processor of a computing device, the executable instructions may cause the computing device to perform a method. The method may include obtaining a request for accessing an image file from a user terminal. The method may include obtaining metadata of the image file based on the request from a first storage device. The method may also include obtaining access information of at least one second storage device that stores image data of the image file based on the metadata from the first storage device. The method may also include obtaining at least one sub-image data set of the image data from the at least one second storage device. The method may further include obtaining the image file by combining the metadata and the at least one sub-image data set.

According to yet another aspect of the present disclosure, a non-transitory computer readable medium may be provided. The non-transitory computer readable may include executable instructions for archiving data. When executed by at least one processor of a computing device, the executable instructions may cause the computing device to perform a method. The method may include obtaining an image file. The method may include storing image data of the image file onto at least one storage device. The method may also include obtaining access information of the image data stored on the at least one storage device. The method may further include generating metadata of the image file based on the access information of the image data.

According to yet another aspect of the present disclosure, a non-transitory computer readable medium may be provided. The non-transitory computer readable may include executable instructions for assessing data. When executed by at least one processor of a computing device, the executable instructions may cause the computing device to perform a method. The method may include obtaining a request for accessing image data of an image file from a user terminal. The method may also include obtaining metadata of the image data based on the request. The method may further include obtaining the image data by accessing at least one storage device based on the metadata.

According to yet another aspect of the present disclosure, a non-transitory computer readable medium may be provided. The non-transitory computer readable may include executable instructions for determining index information. When executed by at least one processor of a computing device, the executable instructions may cause the computing device to perform a method. The method may include obtaining a plurality of image slices. The method may include identifying a series instance unique identifier (UID) of the plurality of image slices. The method may include determining index information of the plurality of image slices based on the series instance UID. The index information may include the series instance UID.

According to yet another aspect of the present disclosure, a non-transitory computer readable medium may be provided. The non-transitory computer readable may include executable instructions for assessing data. When executed by at least one processor of a computing device, the executable instructions may cause the computing device to perform a method. The method may include obtaining a series instance UID from a user terminal. The method may include obtaining index information based on the series instance UID. The method may include also determining whether the index information includes a hash value. In response to determining that the index information does not include the hash value, the method may further include obtaining an image identified as the series instance UID.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 2:
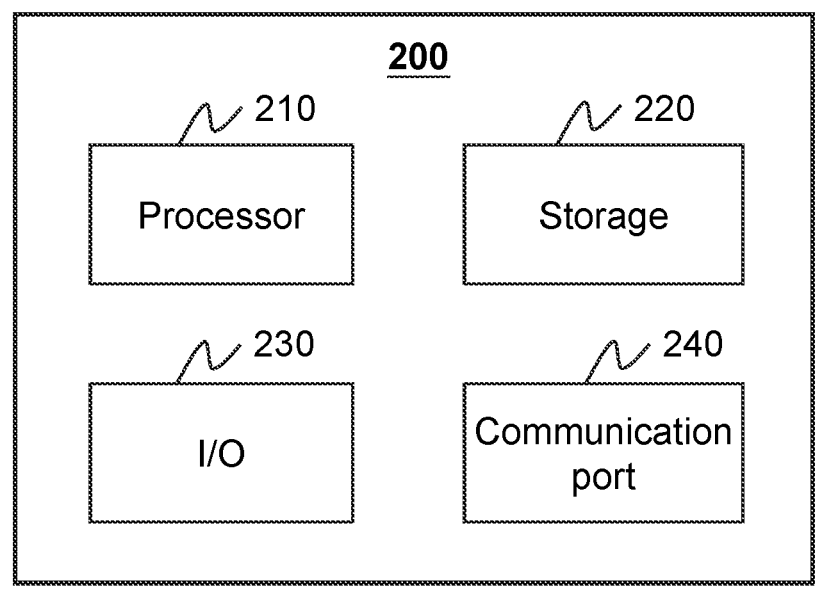
FIG. 2 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. An anatomical structure shown in an image of a subject may correspond to an actual anatomical structure existing in or on the subject's body. The term "segmenting an anatomical structure" or "identifying an anatomical structure" in an image of a subject may refer to segmenting or identifying a portion in the image that corresponds to an actual anatomical structure existing in or on the subject's body. The term "region," "location," and "area" in the present disclosure may refer to a location of an anatomical structure shown in the image or an actual location of the anatomical structure existing in or on the subject's body, since the image may indicate the actual location of a certain anatomical structure existing in or on the subject's body.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for non-invasive biomedical imaging, such as for disease diagnostic or research purposes. In some embodiments, the systems may include a single modality imaging system and/or a multi-modality imaging system. The single modality imaging system may include, for example, an ultrasound imaging system, an X-ray imaging system, an computed tomography (CT) system, a magnetic resonance imaging (MRI) system, an ultrasonography system, a positron emission tomography (PET) system, an optical coherence tomography (OCT) imaging system, an ultrasound (US) imaging system, an intravascular ultrasound (IVUS) imaging system, a near-infrared spectroscopy (NIRS) imaging system, a far-infrared (FIR) imaging system, or the like, or any combination thereof. The multi-modality imaging system may include, for example, an X-ray imaging-magnetic resonance imaging (X-ray-MRI) system, a positron emission tomography-X-ray imaging (PET-X-ray) system, a single-photon emission computed tomography-magnetic resonance imaging (SPECT-MRI) system, a positron emission tomography-computed tomography (PET-CT) system, a C-arm system, a digital subtraction angiography-magnetic resonance imaging (DSA-MRI) system, etc. It should be noted that the imaging system described below is merely provided for illustration purposes, and not intended to limit the scope of the present disclosure.

The term "imaging modality" or "modality" as used herein broadly refers to an imaging method or technology that gathers, generates, processes, and/or analyzes imaging information of a subject. The subject may include a biological subject and/or a non-biological subject. The biological subject may be a human being, an animal, a plant, or a portion thereof (e.g., a heart, a breast, etc.). In some embodiments, the subject may be a man-made composition of organic and/or inorganic matters that are with or without life.

An aspect of the present disclosure relates to systems and methods for data storage. The systems may include a receiving module, a metadata storage module, a segmentation module, and at least one image data storage module. The receiving module may be configured to obtain an image file and divide the image file into metadata (or referred to as a metadata file) and image data. The metadata storage module may be configured to store the metadata of the image file. The segmentation module may be configured to divide image data of the image file into at least one sub-image data set. The at least one image data storage module may be configured to receive and store the at least one sub-image data set.

Conventionally, when an image file is uploaded to a cloud server, the cloud server encrypts and store all data of the image file. When a user needs to obtain the stored data, the user directly downloads the all data of the image file from the cloud server. According to some embodiments of the present disclosure, the image file may be divided into the metadata and the image data. The metadata and the image data may be stored in different devices (e.g., stored in the metadata storage module and the at least one image data storage module, respectively). Moreover, the segmentation module may divide the image data of the image file into at least one sub-image data set and send the at least one sub-image data set to the at least one image data storage module for storage (or referred to as archiving). In this way, the efficiency and/or reliability of the transmission and/or archiving of the image file and the security of image file storage may be improved. Different components (e.g., the metadata, the image data, etc.) of the image file are stored in different devices, which may be separately maintained. Further, by way of separately storing the image data and the metadata, the image data may be compressed using a compression algorithm with a high compression ratio, thereby saving the amount of storage space the image data occupies.

Figure 1:
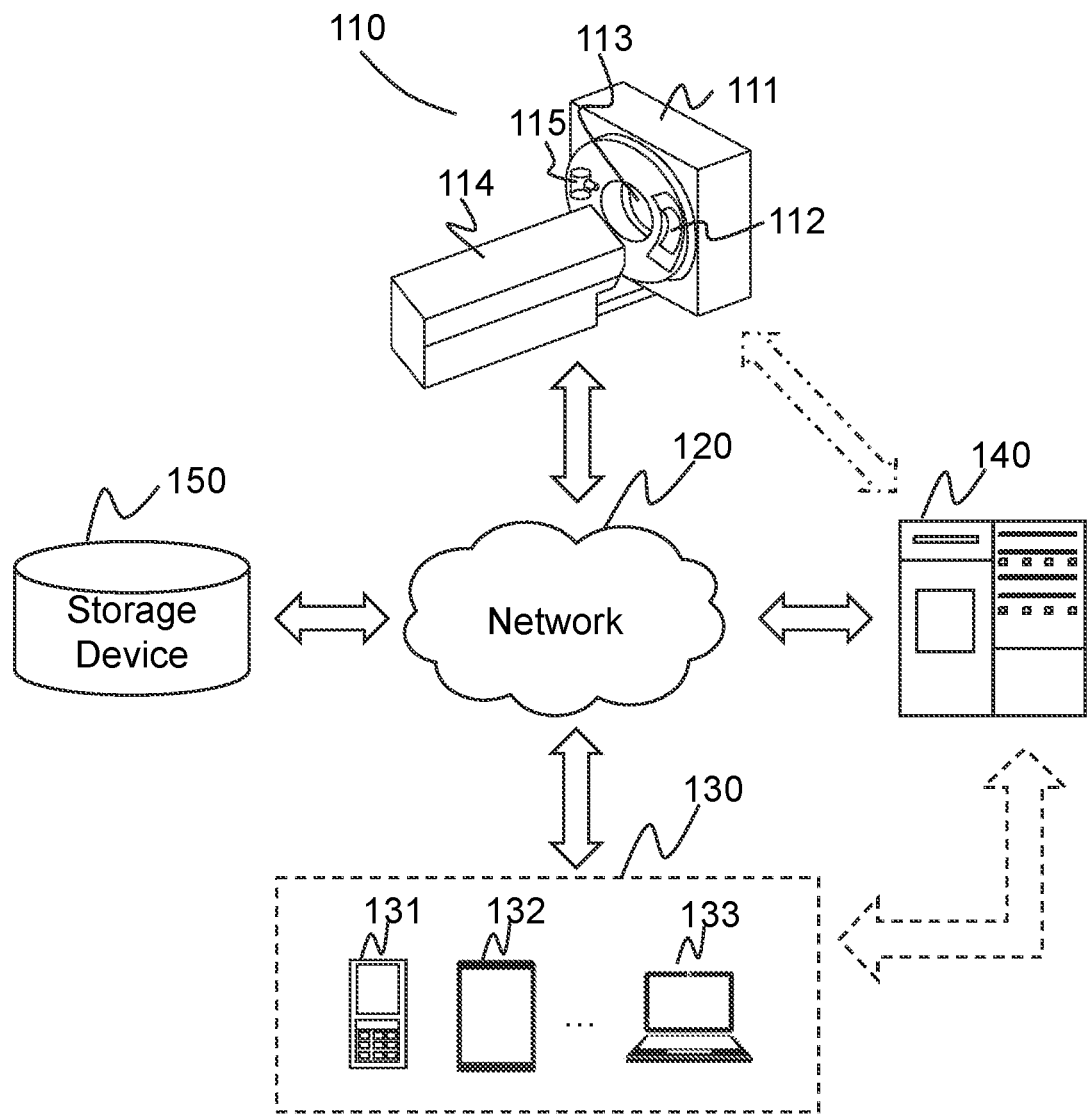
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. As shown, the imaging system 100 may include an imaging device 110, a network 120, one or more terminals 130, a processing device 140, and a storage device 150. In some embodiments, the imaging device 110, the terminal(s) 130, the processing device 140, and/or the storage device 150 may be connected to and/or communicate with each other via a wireless connection (e.g., the network 120), a wired connection, or a combination thereof. The connection between the components of the imaging system 100 may be variable. Merely by way of example, the imaging device 110 may be connected to the processing device 140 through the network 120, as illustrated in FIG. 1. As another example, the imaging device 110 may be connected to the processing device 140 directly or through the network 120. As a further example, the storage device 150 may be connected to the processing device 140 through the network 120 or directly.

The imaging device 110 may generate or provide image data related to a subject via scanning the subject. In some embodiments, the subject may include a biological subject and/or a non-biological subject. For example, the subject may include a specific portion of a body, such as a heart, a breast, or the like. In some embodiments, the imaging device 110 may include a single-modality scanner (e.g., an MRI device, a CT scanner) and/or multi-modality scanner (e.g., a PET-MRI scanner) as described elsewhere in this disclosure. In some embodiments, the image data relating to the subject may include projection data, one or more images of the subject, etc. The projection data may include raw data generated by the imaging device 110 by scanning the subject and/or data generated by a forward projection on an image of the subject.

In some embodiments, the imaging device 110 may include a gantry 111, a detector 112, a detection region 113, a scanning table 114, and a radioactive scanning source 115. The gantry 111 may support the detector 112 and the radioactive scanning source 115. The subject may be placed on the scanning table 114 to be scanned. The radioactive scanning source 115 may emit radioactive rays to the subject. The radiation may include a particle ray, a photon ray, or the like, or a combination thereof. In some embodiments, the radiation may include a plurality of radiation particles (e.g., neutrons, protons, electrons, p-mesons, heavy ions), a plurality of radiation photons (e.g., X-ray, a g-ray, ultraviolet, laser), or the like, or a combination thereof. The detector 112 may detect radiations and/or radiation events (e.g., gamma photons) emitted from the detection region 113. In some embodiments, the detector 112 may include a plurality of detector units. The detector units may include a scintillation detector (e.g., a cesium iodide detector) or a gas detector. The detector unit may be a single-row detector or a multi-rows detector.

The network 120 may include any suitable network that can facilitate the exchange of information and/or data for the imaging system 100. In some embodiments, one or more components of the imaging system 100 (e.g., the imaging device 110, the processing device 140, the storage device 150, the terminal(s) 130) may communicate information and/or data with one or more other components of the imaging system 100 via the network 120. For example, the processing device 140 may obtain image data from the imaging device 110 via the network 120. As another example, the processing device 140 may obtain user instruction(s) from the terminal(s) 130 via the network 120.

The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may be connected to and/or communicate with the imaging device 110, the processing device 140, and/or the storage device 150. In some embodiments, the terminal(s) 130 may include a mobile device 131, a tablet computer 132, a laptop computer 133, or the like, or any combination thereof. For example, the mobile device 131 may include a mobile phone, a personal digital assistant (PDA), a gaming device, a navigation device, a point of sale (POS) device, a laptop, a tablet computer, a desktop, or the like, or any combination thereof. In some embodiments, the terminal(s) 130 may include an input device, an output device, etc. In some embodiments, the terminal(s) 130 may be part of the processing device 140.

The processing device 140 may process data and/or information obtained from the imaging device 110, the storage device 150, the terminal(s) 130, or other components of the imaging system 100. For example, the processing device 140 may store metadata of an image file obtained by the imaging device 110 onto a first storage device. The processing device 140 may divide image data of the image file into at least one sub-image data set. The processing device 140 may also store each sub-image data set of the at least one sub-image data set onto a second storage device of at least one second storage device. The processing device 140 may further store access information of the at least one second storage device onto the first storage device. As another example, the processing device 140 may obtain a request for accessing an image file from the user terminal(s) 130. The processing device 140 may also obtain metadata of the image file based on the request from a first storage device and access information of at least one second storage device that stores image data of the image file based on the metadata from the first storage device. The processing device 140 may also obtain at least one sub-image data set of the image data from the at least one second storage device. The processing device 140 may further obtain the image file by combining the metadata and the at least one sub-image data set.

In some embodiments, the processing device 140 may be a single server or a server group. The server group may be centralized or distributed. In some embodiments, the processing device 140 may be local to or remote from the imaging system 100. For example, the processing device 140 may access information and/or data from the imaging device 110, the storage device 150, and/or the terminal(s) 130 via the network 120. As another example, the processing device 140 may be directly connected to the imaging device 110, the terminal(s) 130, and/or the storage device 150 to access information and/or data. In some embodiments, the processing device 140 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 140 may be implemented by a computing device 200 having one or more components as described in connection with FIG. 2.

In some embodiments, the processing device 140 may include one or more processors (e.g., single-core processor(s) or multi-core processor(s)). Merely by way of example, the processing device 140 may include a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

The storage device 150 may store data, instructions, and/or any other information. In some embodiments, the storage device 150 may store data obtained from the processing device 140, the terminal(s) 130, and/or the imaging device 110. For example, the storage device 150 may store image data collected by the imaging device 110. As another example, the storage device 150 may store image files (or a portion thereof, or information relating to the image files). In some embodiments, the storage device 150 may store data and/or executable instructions that the processing device 140 may execute or use to perform exemplary methods described in the present disclosure. For example, the storage device 150 may store data and/or executable instructions that the processing device 140 may execute or use for image processing.

In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure.

In some embodiments, the storage device 150 may be connected to the network 120 to communicate with one or more other components of the imaging system 100 (e.g., the processing device 140, the terminal(s) 130). One or more components of the imaging system 100 may access the data or executable instructions stored in the storage device 150 via the network 120. In some embodiments, the storage device 150 may be part of the processing device 140. It should be noted that the description of only one storage device 150 is illustrative, and not intended to limit the scope of the present disclosure. For example, the imaging system 100 may include a plurality of storage devices, each of which may be configured to store information or executable instructions.

It should be noted that the above description of the imaging system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the imaging system 100 may include one or more additional components. Additionally or alternatively, one or more components of the imaging system 100 described above may be omitted. As another example, two or more components of the imaging system 100 may be integrated into a single component.

FIG. 2 is a schematic diagram illustrating exemplary hardware and/or software components of a computing device 200 according to some embodiments of the present disclosure. The computing device 200 may be used to implement any component of the imaging system 100 as described herein. For example, the processing device 140 and/or the terminal(s) 130 may be implemented on the computing device 200, respectively, via its hardware, software program, firmware, or a combination thereof. Although only one such computing device is shown, for convenience, the computer functions relating to the imaging system 100 as described herein may be implemented in a distributed fashion on a number of similar platforms, to distribute the processing load. As illustrated in FIG. 2, the computing device 200 may include a processor 210, a storage device 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the imaging device 110, the terminal(s) 130, the storage device 150, and/or any other component of the imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage device 220 may store data/information obtained from the imaging device 110, the terminal(s) 130, the storage device 150, and/or any other component of the imaging system 100. In some embodiments, the storage device 220 may include a mass storage device, a removable storage device, a volatile read-and-write memory, a read-only memory (ROM), or the like, or any combination thereof. In some embodiments, the storage device 220 may store one or more programs and/or instructions to perform exemplary methods described in the present disclosure.

The I/O 230 may input and/or output signals, data, information, etc. In some embodiments, the I/O 230 may enable a user interaction with the processing device 140. In some embodiments, the I/O 230 may include an input device and an output device. The input device may include alpha-numeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 140) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 120) to facilitate data communications. The communication port 240 may establish connections between the processing device 140 and the imaging device 110, the terminal(s) 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
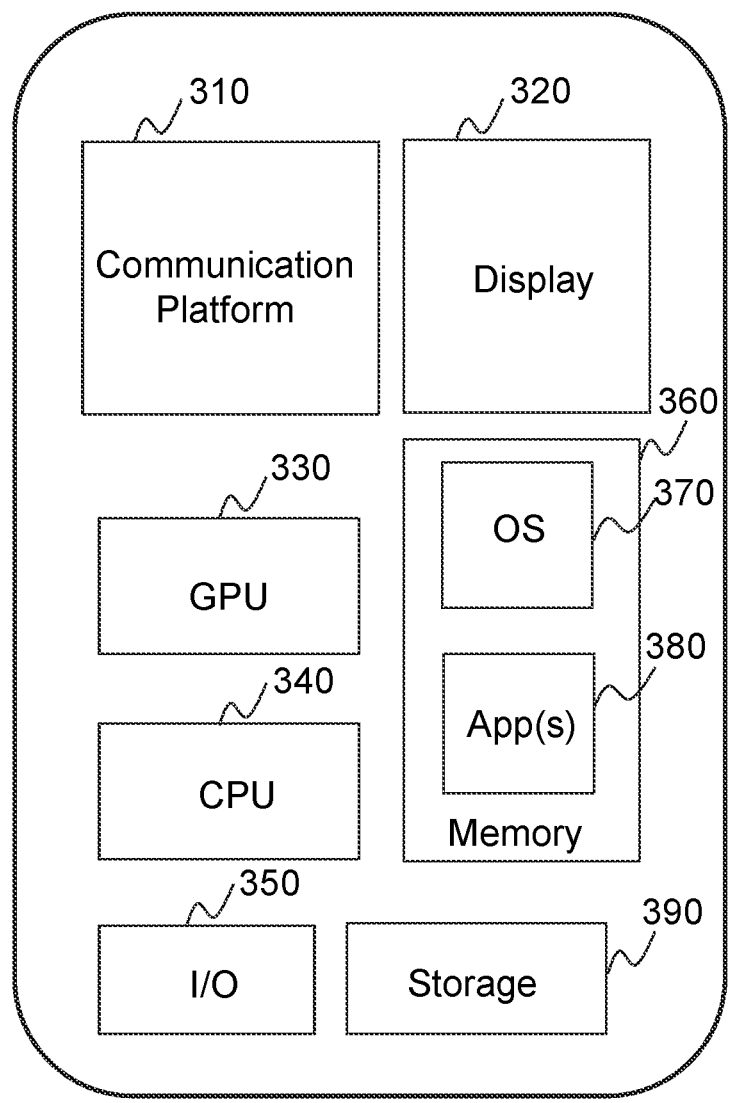
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device 300 according to some embodiments of the present disclosure. In some embodiments, one or more components (e.g., a terminal 130 and/or the processing device 140) of the imaging system 100 may be implemented on the mobile device 300.

As illustrated in FIG. 3, the mobile device 300 may include a communication platform 310, a display 320, a graphics processing unit (GPU) 330, a central processing unit (CPU) 340, an I/O 350, a memory 360, and a storage unit 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
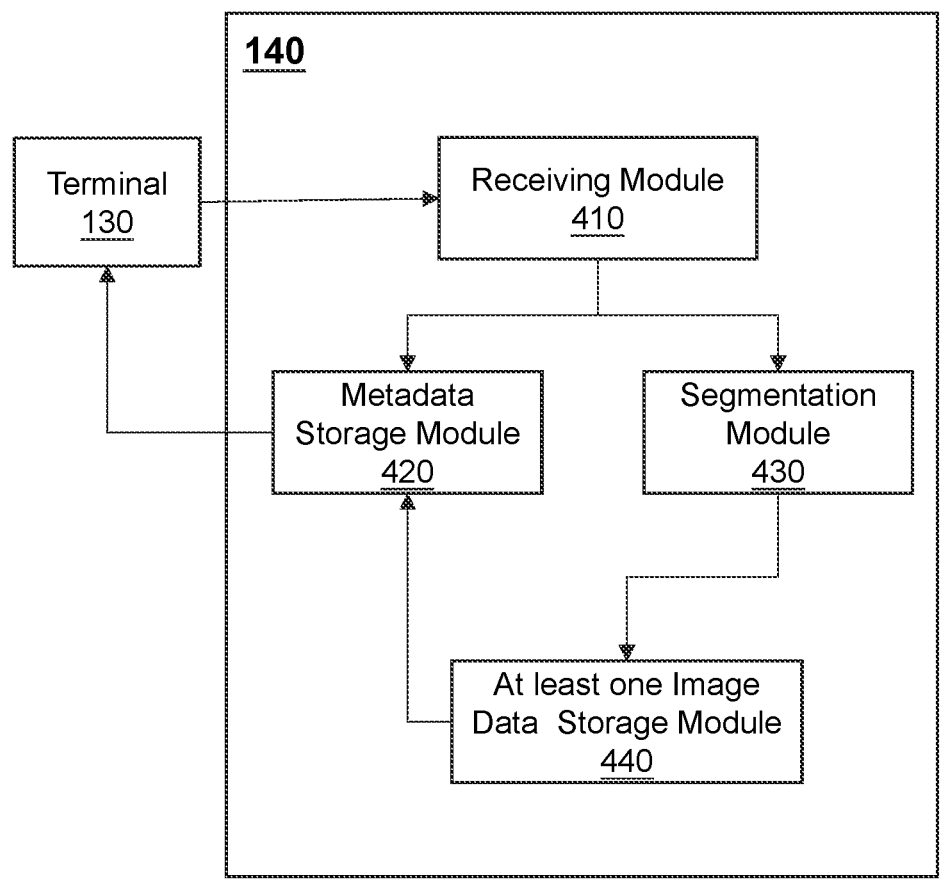
FIG. 4 is a block diagram illustrating an exemplary processing device according to some embodiments of the present disclosure.

FIG. 4 is a block diagram illustrating an exemplary processing device 140 according to some embodiments of the present disclosure. In some embodiments, the processing device 140 may be implemented on a processing unit (e.g., a processor 210 illustrated in FIG. 2 or a CPU 340 as illustrated in FIG. 3). As shown in FIG. 4, the processing device 140 may include a receiving module 410, a metadata storage module 420, a segmentation module 430, and at least one image data storage module 440.

The receiving module 410 may be configured to receive/obtain an image file from a terminal 130 (e.g., the imaging device 110 of the imaging system 100) or an external device (e.g., a user terminal). In some embodiments, the image file may be a medical image file (e.g., a digital imaging communication in medicine (DICOM) file) of a subject generated using an imaging device as described elsewhere in this disclosure. As used herein, the subject may include a biological subject and/or a non-biological subject. For example, the subject may be a human being, an animal, or a portion thereof. As another example, the subject may be a phantom. In some embodiments, the subject may be a patient, or a portion of the patient (e.g., the chest, a breast, and/or the abdomen of the patient). In some embodiments, the image file may include a plurality of image slices. More descriptions for storing and/or accessing the plurality of image slices may be found elsewhere (e.g., FIGS. 17-22 and the descriptions thereof) in the present disclosure.

In some embodiments, the image file may include metadata (or referred to as a metadata file) and image data. The metadata may be configured to provide information about the image data or the image file. For example, the metadata may include a name of the image file, a size of the image file, a timestamp of the image file, a service-object pair (SOP) class unique identifier (UID), an SOP instance UID, a study instance UID, a series instance UID, a patient ID, a patient name, a date of birth of a patient, a description of an illness of a patient, or the like, or any combination thereof. In some embodiments, the metadata may include at least one level of information. For example, the metadata may include a first level of information relating to the subject, a second level of information relating to examinations that the subject has made, a third level of information relating to series of the image data, and a fourth level of information relating to the image data.

The image data may include volume data, voxel data, pixel data, etc. In some embodiments, the image data may be medical image data. For example, the image data may include MR image data, PET image data, CT image data, PET-CT image data, PET-MR image data, ultrasound image data, etc., obtained from the imaging device 110 (e.g., a CT device, an MRI device, an X-ray device, a PET device, etc.).

In some embodiments, the receiving module 410 may obtain the image data from the imaging device 110. In some embodiments, the image data may be previously generated and stored in a storage device (e.g., the storage device 150, the storage device 220, the storage 390, or an external source). The receiving module 410 may retrieve the image data from the storage device.

In some embodiments, after the image file is obtained, the receiving module 410 may divide the image file into the metadata and the image data. For example, the receiving module 410 may parse the image file according to a parsing algorithm (e.g., a machine learning algorithm, etc.). The receiving module 410 may further send the metadata to the metadata storage module 420 and the image data to the segmentation module 430, respectively.

The metadata storage module 420 may be configured to store the metadata of the image file. In some embodiments, the metadata storage module 420 may encrypt the metadata of the image file to obtain the encrypted metadata. For example, the metadata storage module 420 may encrypt the metadata of the image file using a data encryption algorithm. Exemplary data encryption algorithms may include an advanced encryption standard (AES) algorithm, a Diffie-Hellman algorithm, etc. The metadata storage module 420 may further store the encrypted metadata of the image file.

The segmentation module 430 may be configured to divide the image data of the image file into at least one sub-image data set and send the at least one sub-image data set to the at least one image data storage module 440. In some embodiments, the segmentation module 430 may divide the image data of the image file into the at least one sub-image data set based on a file size threshold. The file size threshold may indicate a maximum size of a sub-image data set. In some embodiments, the file size threshold may be set manually by a user (e.g., an engineer) according to an experience value or a default setting of the imaging system 100, or determined by the processing device 140 according to an actual need.

In some embodiments, the segmentation module 430 may encode the at least one sub-image data set to obtain at least one encoded sub-image data set and an identifier of each of the at least one encoded sub-image data set. Exemplary encoding algorithms may include a lossy encoding algorithm (e.g., a discrete Cosine Transform algorithm, a fractal compression algorithm, etc.), a lossless encoding algorithm (e.g., a run length encoding algorithm, a Lempel-Ziv-Welch algorithm, a Huffman coding algorithm, a Fano Shannon encoding algorithm, an arithmetic coding algorithm, etc.). The segmentation module 430 may further send the at least one encoded sub-image data set and the identifier of each of the at least one encoded sub-image data set to the at least one image data storage module 440.

In some embodiments, the receiving module 410, the metadata storage module 420, and the segmentation module 430 may be implemented on different servers, respectively, to form a server cluster. Alternatively, the receiving module 410, the metadata storage module 420, and the segmentation module 430 may be implemented on a same server.

The at least one image data storage module 440 may be configured to receive and store the at least one sub-image data set. In some embodiments, to improve the fault-tolerant ability for storing the image data, each of the at least on image data storage module 440 may store one or more of the at least one sub-image data set, so that all of the at least one sub-image data set is not stored in a same image data storage device. In some embodiments, the at least on image data storage module 440 may be implemented on different servers, respectively, to form a server cluster. Alternatively, the at least one image data storage module 440 may be implemented on a same server.

In some embodiments, the at least one image data storage module 440 may receive and store the at least one encoded sub-image data set. After the at least one encoded sub-image data set being stored in the at least one image data storage module 440, an identifier of each of the at least one encoded sub-image data set and/or access information (e.g., an IP address) of the at least one image data storage module 440 that stores the at least one encoded sub-image data set may be sent by the segmentation module 430.

In some embodiments, the at least one image data storage module 440 may send the identifier of each of the at least one encoded sub-image data set and access information (e.g., an IP address) of the at least one image data storage module 440 to the metadata storage module 420.

In some embodiments, the metadata storage module 420 may correlate (and store) the identify of each of the at least one encoded sub-image data set, the access information of the at least one image data storage module 440, and the metadata. In some embodiments, the metadata storage module 420 may update the metadata based on the identifier of each of the at least one encoded sub-image data set and access information (e.g., an IP address) of the at least one image data storage module 440. Merely by way of example, the metadata storage module 420 may determine (or update) the metadata corresponding to the at least one encoded sub-image data set based on the identifier of each of the at least one encoded sub-image data set. The metadata corresponding to the at least one encoded sub-image data set may be associated with the identifier of the at least one encoded sub-image data set and the access information of at least one image data storage module 440 and stored in the metadata storage module 420 to facilitate the retrieval of image file in the future. More descriptions for the generating of metadata based on the access information of the at least one second storage device may be found elsewhere in the present disclosure (e.g., FIGS. 11-14 and the descriptions thereof).

In some embodiments, after the metadata, the identifier of the at least one encoded sub-image data set, and/or the access information of at least one image data storage module 440 are stored in the metadata storage module 420, the metadata storage module 420 may send a message, to a terminal 130, indicating that the storage of the image file is completed.

Usually, the metadata includes private information of the subject and an occupied storage space of the metadata is less than that of the image data. According to some embodiments of the present disclosure, after the image file is obtained, the receiving module 410 encrypts the metadata to avoid the leakage of the private information of the subject, which may improve the efficiency and/or reliability of the storage of the image file. In addition, the segmentation module 430 divides the image data of the image file into at least one sub-image data set and sends the at least one sub-image data set to the at least one image data storage module 440 for storage, thereby improving the efficiency and/or reliability of the storage of the image file and the security of image file storage by reducing the leakage of all image data. The encoding of the image data (or the at least one sub-image data set) may increase security of the image data storage.

Figure 5:
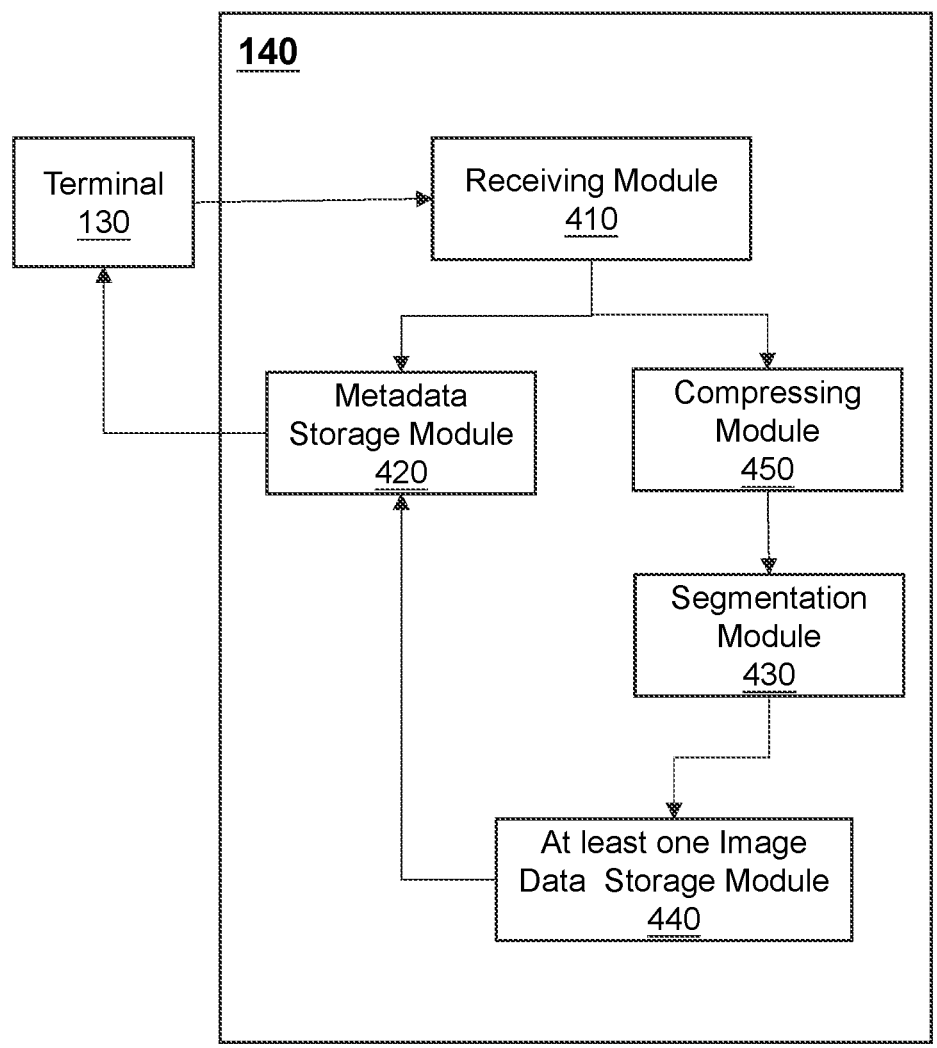
FIG. 5 is a block diagram illustrating an exemplary processing device according to some embodiments of the present disclosure.

FIG. 5 is a block diagram illustrating an exemplary processing device 140 according to some embodiments of the present disclosure. In some embodiments, the processing device 140 may be implemented on a processing unit (e.g., a processor 210 illustrated in FIG. 2 or a CPU 340 as illustrated in FIG. 3).

As shown in FIG. 5, on the basis of the processing device 140 illustrated in FIG. 4, the processing device 140 may further include a compressing module 450.

The compressing module 450 may be configured to compress the image data of the image file to obtain compressed image data and send the compressed image data to the segmentation module 430. The segmentation module 430 may further divide the compressed image data into the at least one sub-image data set.

In some embodiments, the compressing module 450 may be implemented on an individual server to configured to compressed the image data. Alternatively, the compressing module 450 and the segmentation module 430 may be implemented on a same server, so that the image data is compressed and divided.

According to some embodiments of the present disclosure, when the terminal 130 obtains the image file, the terminal 130 may send the image file to the receiving module 410. The receiving module 410 may divide the image file into the metadata and the image data. The receiving module 410 may further send the metadata to the metadata storage module 420 and the image data to the compressing module 450. The compressing module 450 may compress the image data of the image file using a compression algorithm with a high compression ratio to obtain the compressed image data and send the compressed image data to the segmentation module 430. Exemplary compression algorithm may include JPEG Lossless algorithm. The segmentation module 430 may divide the compressed image data of the image file into at least one sub-image data set and encode the at least one sub-image data set to obtain at least one encoded sub-image data set. An identifier of each of the at least one encoded sub-image data set may be obtained. The segmentation module 430 may further send the at least one encoded sub-image data set and/or the identifier of each of the at least one encoded sub-image data set to the at least one image data storage module 440 for storage. In this way, the storage space for storing the image data may be effectively reduced by compressing the image data using the compression algorithm with the high compression ratio. In addition, the segmentation module 430 may divide the compressed image data into at least one sub-image data set and send the at least one sub-image data set to the at least one image data storage module 440 for storage, which may reduce the leakage of all image data, thereby improving the security of image file storage.

Figure 6:
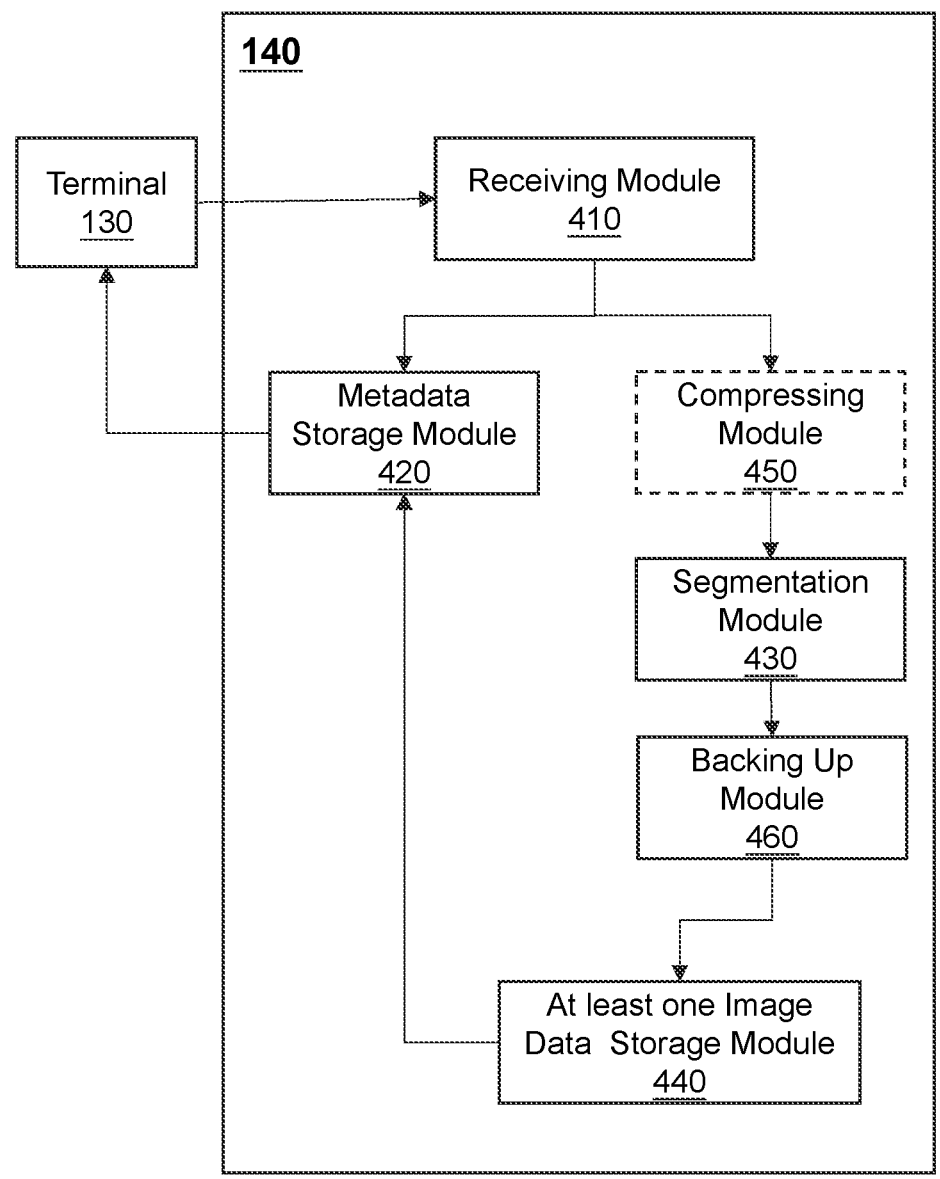
FIG. 6 is a block diagram illustrating an exemplary processing device according to some embodiments of the present disclosure.

FIG. 6 is a block diagram illustrating an exemplary processing device 140 according to some embodiments of the present disclosure. In some embodiments, the processing device 140 may be implemented on a processing unit (e.g., a processor 210 illustrated in FIG. 2 or a CPU 340 as illustrated in FIG. 3).

As shown in FIG. 6, on the basis of the processing device 140 illustrated in FIG. 4 and/or the processing device 140 illustrated in FIG. 5, the processing device 140 may further include a backing up module 460. The backing up module 460 may be configured to back up the at least one sub-image data set based on a predetermined backup count (e.g., one, two, three, four, etc.) to obtain a plurality of backup files for each of the at least one sub-image data set. The backing up module 460 may further send the plurality of backup files to the at least one image data storage module 440 for storage. The predetermined backup count may be determined according to a degree of importance of the image file. For example, the more important of the image file, the greater of the predetermined backup count.

In some embodiments, the backing up module 460 may be implemented on an individual server for backing up the at least one sub-image data set. Alternatively, the backing up module 460 and the segmentation module 430 may be implemented on a same server, so that the image data is divided and backed up.

According to some embodiments of the present disclosure, when the terminal 130 obtains the image file, the terminal 130 may send the image file to the receiving module 410. The receiving module 410 may divide the image file into the metadata and the image data. The receiving module 410 may further send the metadata to the metadata storage module 420 and the image data to the segmentation module 430. The segmentation module 430 may divide the image data of the image file into at least one sub-image data set and encode the at least one sub-image data set to obtain at least one encoded sub-image data set. An identifier of each of the at least one encoded sub-image data set may be obtained. The segmentation module 430 may further send the at least one encoded sub-image data set and/or the identifier of each of the at least one encoded sub-image data set to the backing up module 460. The backing up module 460 may back up the at least one sub-image data set based on a predetermined backup count to obtain a plurality of backup files for each of the at least one sub-image data set. The backing up module 460 may further send the plurality of backup files and the identifier of each of the plurality of backup files to the at least one image data storage module 440 for storage. In this way, the security of the image data may be effectively improved by backing up the image data.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the metadata storage module 420 and/or the at least one image data storage module 440 may be storage devices out of the processing device 140. As another example, the processing device 140 described in FIGS. 4-6 may further include an editing module. The editing module may be configured to edit at least a portion of the image file. For example, the editing module may modify, update, or delete the at least a portion of the image file, and update the metadata of the image file. For example, the editing module may obtain access information of at least one image data storage module 440 that stores image data (or a portion thereof), access the at least one image data storage module 440 based on the access information, and update (or modify, or delete) the pre-stored image data.

Figure 7A:
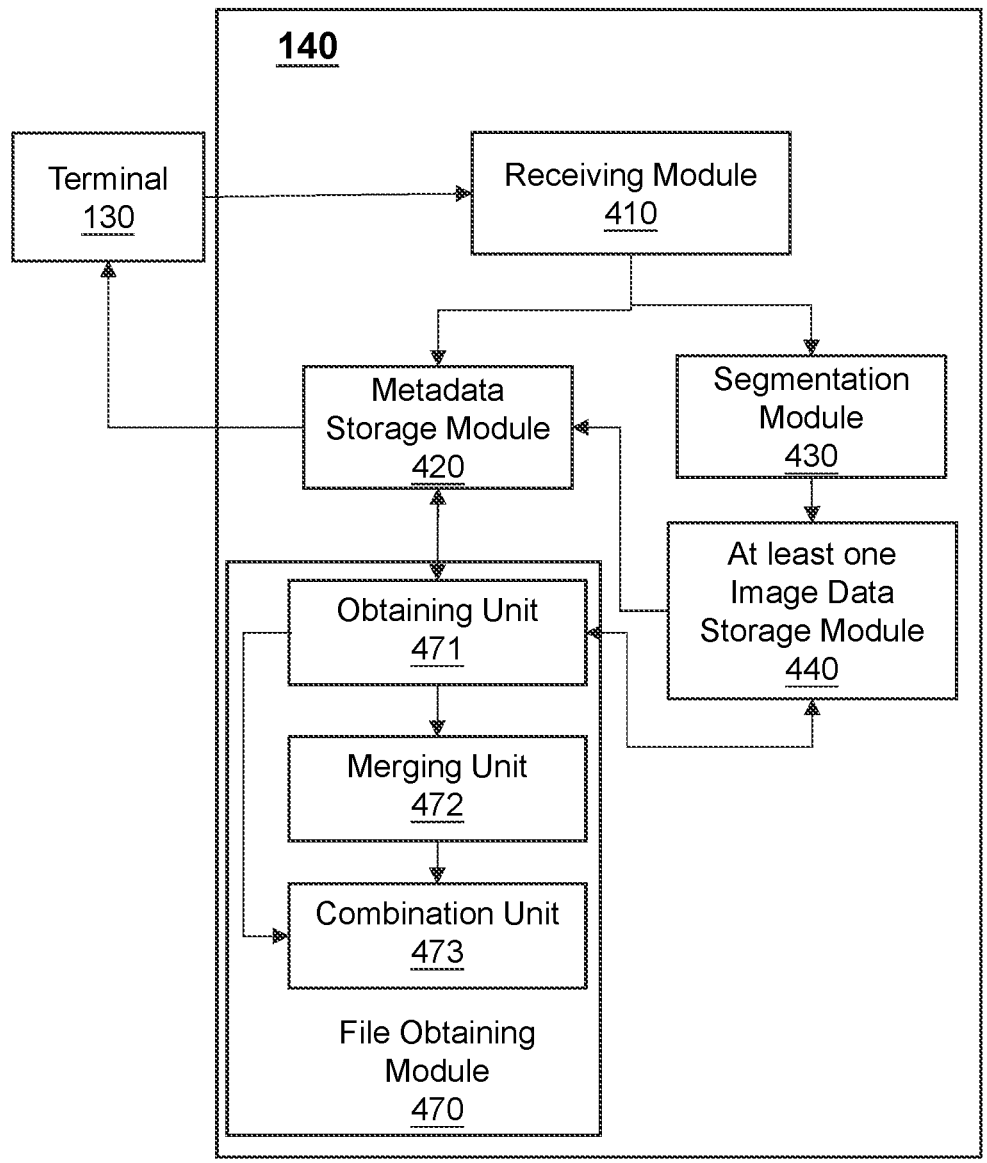
FIG. 7A is a block diagram illustrating an exemplary processing device according to some embodiments of the present disclosure.
Figure 7B:
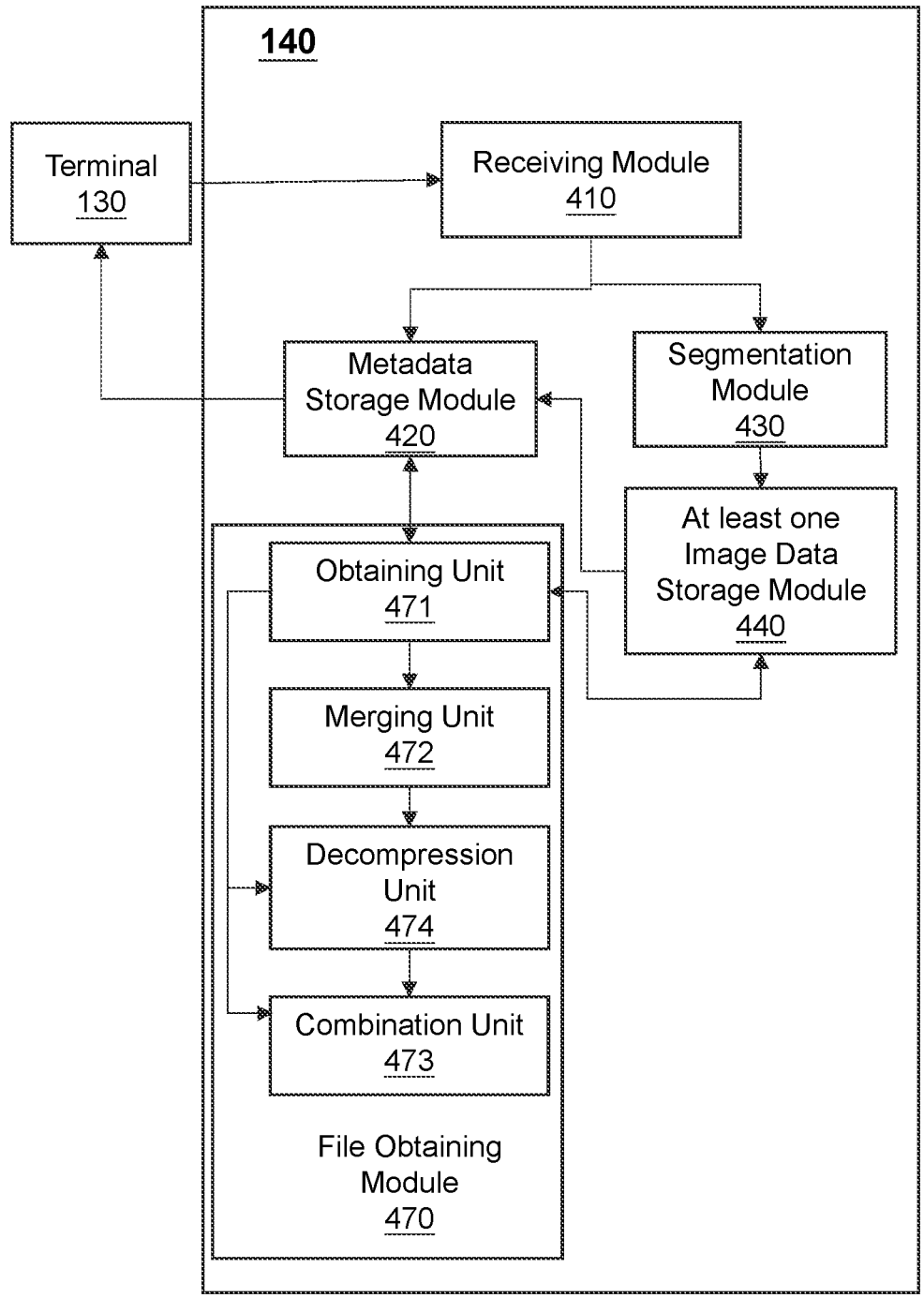
FIG. 7B is a block diagram illustrating an exemplary processing device according to some embodiments of the present disclosure.

FIG. 7A is a block diagram illustrating an exemplary processing device 140 according to some embodiments of the present disclosure. FIG. 7B is a block diagram illustrating an exemplary processing device 140 according to some embodiments of the present disclosure. In some embodiments, the processing device 140 may be implemented on a processing unit (e.g., a processor 210 illustrated in FIG. 2 or a CPU 340 as illustrated in FIG. 3).

As shown in FIG. 7A, on the basis of the processing device 140 illustrated in FIG. 4, the processing device 140 may further include a file obtaining module 470. The file obtaining module 470 may be configured to obtain an image file (or referred to as a target image file). The file obtaining module 470 may receive a request for obtaining the target image file. The file obtaining module 470 may obtain, from the metadata storage module 420, metadata of the target image file based on the request. The file obtaining module 470 may obtain, from the at least one image data storage module 440, image data of the target image file based on the metadata of the target image file. The file obtaining module 470 may obtain the target image file based on the image data and the metadata of the target image file.

In some embodiments, the file obtaining module 470 may include an obtaining unit 471, a merging unit 472, and a combination unit 473.

The obtaining unit 471 may be configured to obtain the request from the terminal 130 and the metadata of the target image file based on the request from the metadata storage module 420. For example, the obtaining unit 471 may obtain an identifier of the metadata of the target file image by parsing the request. The obtaining unit 471 may further obtain, from the metadata storage module 420, the metadata of the target file image based on the identifier corresponding to the metadata of the target file image.

The obtaining unit 471 may be also configured to obtain, from the at least one image data storage module 440, at least one target sub-image data set of the target file image based on the metadata of the target file image. For example, the obtaining unit 471 may obtain an identifier of each of the at least one target sub-image data set and access information of at least one target image data storage module 440 for storing the at least one target sub-image data set based on the metadata of the target file image. The obtaining unit 471 may further obtain the at least one target sub-image data set based on the identifier of each of the at least one target sub-image data set and the access information of the at least one target image data storage module 440 from the at least one target image data storage module 440. The obtaining unit 471 may further send the at least one target sub-image data set to the merging unit 472.

The merging unit 472 may be configured to merge the at least one target sub-image data set of the target image file to generate the image data of the target image file and send the image data of the target image file to the combination unit 473. The combination unit 473 may be configured to combine the image data and the metadata of the target image file to obtain the target image file.

In some embodiments, if the obtained metadata of the target image file by obtaining unit 471 from the metadata storage module 420 is encrypted, before the combination unit 473 combines the image data and the metadata of the target image file, the obtained metadata of the target image file may be decrypted, so that the combination unit 473 may combine the image data and the decrypted metadata of the target image file to obtain the target image file. In this way, the efficiency and/or reliability of the obtaining of the target image file may be improved because that the little occupied storage space of the metadata.

In some embodiments, if the merged image data of the target image file generated by the merging unit 472 is compressed image data, as shown in FIG. 7B, the file obtaining module 470 may further include a decompression unit 474. The decompression unit 474 may be configured to decompress the merged image data of the target image file to obtain the decompressed image data of the target image file and send the decompressed image data of the target image file to the combination unit 473. For example, the decompression unit 474 may decompress the merged image data of the target image file using a decompression algorithm. The decompression algorithm may match with the compression algorithm for compressing the image data of the target image file. The combination unit 473 may combine the decompressed image data and the metadata of the target image file to obtain the target image file.

In some embodiments, the combination unit 473 may send the target image file to the user terminal 130 for browsing. In some embodiments, the merging unit 472 may obtain the metadata of the target image file from the obtaining unit 471. The merging unit 472 may simultaneously or successively send the metadata and the merged image data of the target image file to the user terminal 130. Since the little occupied storage space of the metadata, the metadata may be obtained earlier than the image data. A user may successively browse the metadata and the image data by the terminal 130.

In some embodiments, the obtaining unit 471 may obtain a request for obtaining one or more levels of information of the target image file (e.g., information relating to a subject, examination information of the subject, etc.). The obtaining unit 471 may obtain the identifier corresponding to the metadata of the target file image by parsing the request.

The obtaining unit 471 may obtain, from the metadata storage module 420, the metadata of the target file image based on the identifier corresponding to the metadata of the target file image. The obtaining unit 471 may further obtain the one or more levels of information of the target image file from the metadata of the target image file and send the one or more levels of information of the target image file to the user terminal 130 for browsing. More descriptions for the levels of information may be found elsewhere in the present disclosure (e.g., FIG. 4 and the descriptions thereof).

In some embodiments, the image file includes at least one image slice. The file obtaining module 470 may obtain a series instance UID from a user terminal. The file obtaining module 470 may obtain index information of the at least one image slice based on the series instance UID. As used herein, the index information of the image data refers to a unique identification of the image data generated based on the image data. The file obtaining module 470 may further obtain the at least one image slice based on the index information of the at least one image slice. More descriptions for the obtaining of the at least one image slice may be found elsewhere in the present disclosure (e.g., FIGS. 18, 22 and the descriptions thereof).

Figure 8:
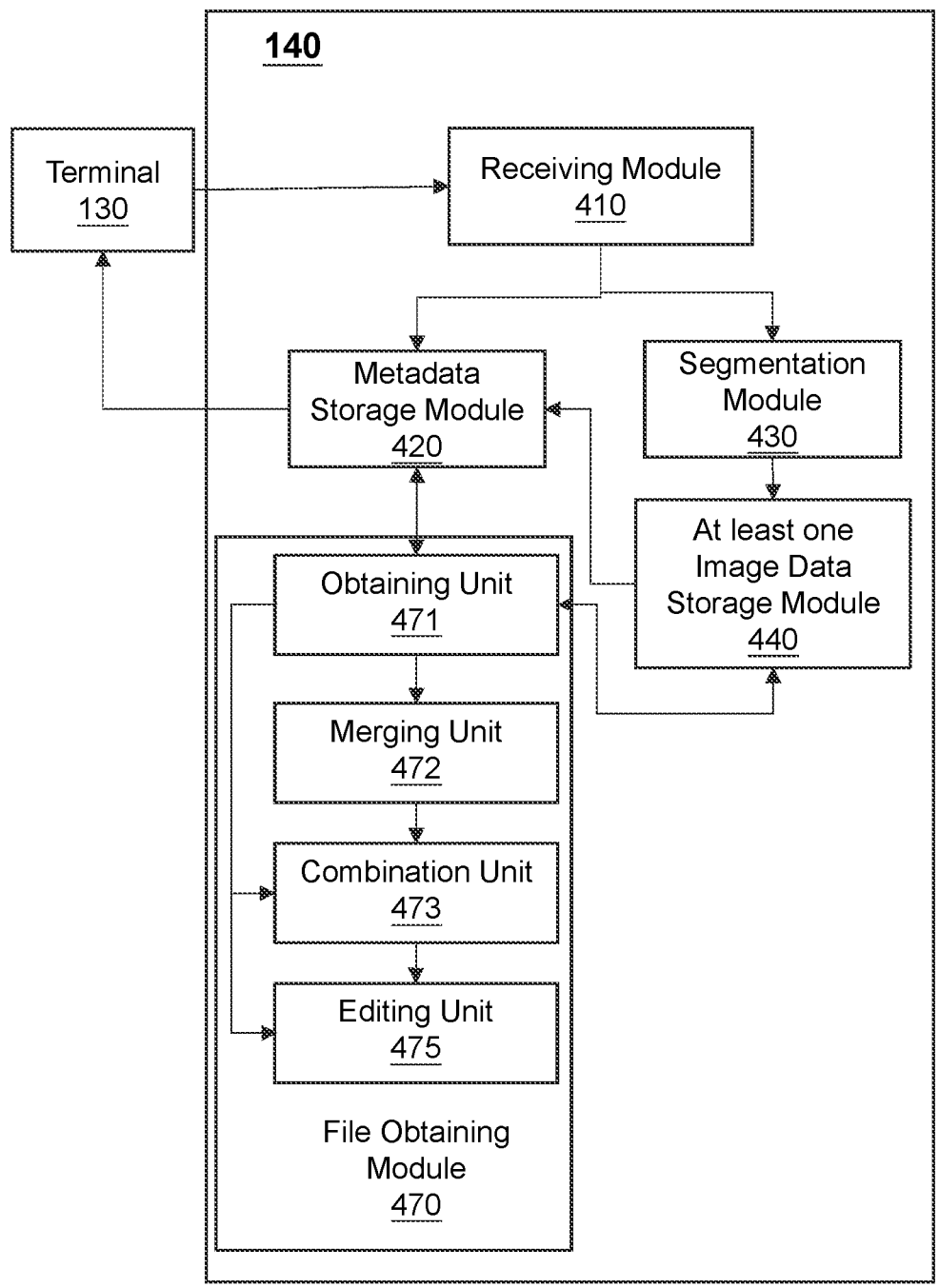
FIG. 8 is a block diagram illustrating an exemplary processing device according to some embodiments of the present disclosure.

FIG. 8 is a block diagram illustrating an exemplary processing device 140 according to some embodiments of the present disclosure. In some embodiments, the processing device 140 may be implemented on a processing unit (e.g., a processor 210 illustrated in FIG. 2 or a CPU 340 as illustrated in FIG. 3).

On the basis of the processing device 140 illustrated in FIG. 7, the file obtaining module 470 of the processing device 140 may be further configured to edit at least a portion of a target image file. In some embodiments, the editing of a target image file (or a portion thereof) may include modifying, updating, or deleting the target image file (or a portion thereof), and update at least a portion of the metadata of the target image file. The file obtaining module 470 of the processing device 140 may receive a request for editing at least a portion of the target image file and edit at least a portion of the target image file based on the request. For example, the file obtaining module 470 may edit the metadata (or a portion thereof) and/or the image data (or a portion thereof) of the target image file.

In some embodiments, as shown in FIG. 8, on the basis of the processing device 140 illustrated in FIG. 7, the file obtaining module 470 140 may further include an editing unit 475. The editing unit 475 may be configured to edit at least a portion of the target image file.

In some embodiments, the obtaining unit 471 may obtain the request for editing the target image file and send the request for editing the target image file to the editing unit 475. The obtaining unit 471, the merging unit 472, and the combination unit 473 may obtain the target image file. More descriptions for the obtaining of the target image file may be found elsewhere in the present disclosure (e.g., FIG. 7 and the descriptions thereof). The combination unit 473 may send the obtained the target image file to the editing unit 475. The editing unit 475 may edit the target image file according to the request for editing the target image file. After the target image file is edited, the processing device 140 may store the edited target image file and delete the original target image file. More descriptions for the storage of the edited target image file may be found elsewhere in the present disclosure (e.g., FIGS. 4-6 and the descriptions thereof).

In some embodiments, if the request for editing the target image file indicates that the metadata of the target image file needs to be edited, the obtaining unit 471 may obtain the request for editing the target image file. The obtaining unit 471 may obtain the metadata of the target image file based on the request for editing the target image file. For example, the obtaining unit 471 may obtain, from the metadata storage module 420, the identifier corresponding to the metadata of the target image file by parsing the request for editing the target image file. The obtaining unit 471 may further obtain the metadata of the target image file based on the identifier corresponding to the metadata of the target image file from the metadata storage module 420. The obtaining unit 471 may send the request for editing the target image file and the metadata of the target image file to the editing unit 475. The editing unit 475 may edit the metadata of the target image file based on the request for editing the target image file. After the metadata of the target image file is edited, the editing unit 475 may send the edited metadata of the target image file to the metadata storage module 420 for replacing the original metadata of the target image file.

In some embodiments, if the request for editing the target image file indicates that a target sub-image data set of the target image file needs to be edited, the obtaining unit 471 may obtain the request for editing the target image file. The obtaining unit 471 may obtain the metadata of the target image file based on the request for editing the target image file. The obtaining unit 471 may further obtain the target sub-image data set of the target image file based on the metadata of the target image file from an image data storage module 440 for storing the target sub-image data set. The obtaining unit 471 may send the request for editing the target image file and the target sub-image data set of the target image file to the editing unit 475. The editing unit 475 may edit the target sub-image data set of the target image file based on the request for editing the target image file. After the target sub-image data set of the target image file is edited, the editing unit 475 may send the edited the target sub-image data set of the target image file to the image data storage module 440 for storing the target sub-image data set for replacing the original sub-image data set of the target image file. More descriptions for the editing of the image file may be found elsewhere in the present disclosure (e.g., FIG. 16 and the descriptions thereof).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the receiving module 410 may divide the image file into the metadata and the image data and send the metadata and the image data to the metadata storage module 420. The metadata storage module 420 may send the image data to the segmentation module 430.

Figure 9:
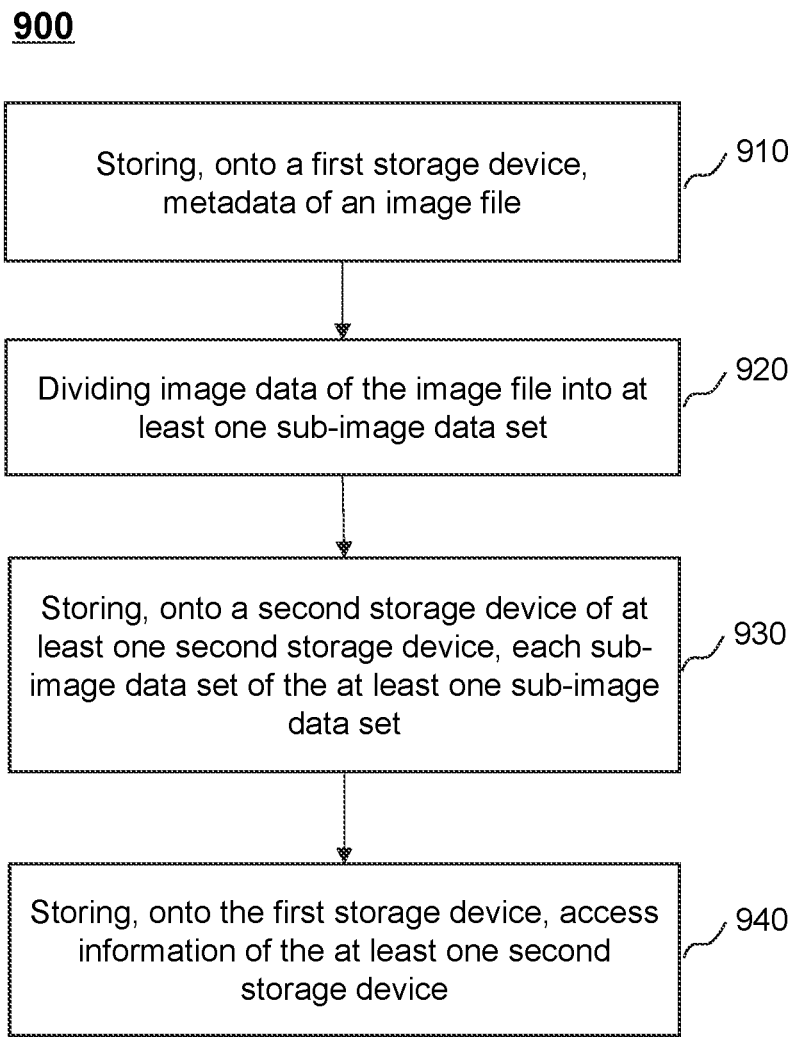
FIG. 9 is a flowchart illustrating an exemplary process for data storage according to some embodiments of the present disclosure.

FIG. 9 is a flowchart illustrating an exemplary process 900 for data storage according to some embodiments of the present disclosure. In some embodiments, the process 900 may be implemented in the imaging system 100 illustrated in FIG. 1. For example, the process 900 may be stored in a storage (e.g., the storage device 150, the storage device 220, the storage 390) as a form of instructions, and invoked and/or executed by the processing device 140 (e.g., the processor 210 of the computing device 200 as illustrated in FIG. 2, the CPU 340 of the mobile device 300 as illustrated in FIG. 3, and/or one or more modules as illustrated in FIGS. 4-8). The operations of the illustrated process presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting.

In 910, the processing device 140 may store, onto a first storage device, metadata of an image file.

In some embodiments, the processing device 140 may obtain the image file from an imaging device (e.g., the imaging device 110 of the imaging system 100) or an external device (e.g., a terminal 130). In some embodiments, the image file may include the metadata and image data of the image file. More descriptions for the metadata and image data of the image file may be found elsewhere in the present disclosure (e.g., FIG. 4 and the descriptions thereof).

In some embodiments, the processing device 140 may divide the image file into the metadata and the image data of the of the image file. The processing device 140 may further store the metadata of the image file onto the first storage device (e.g., the metadata storage module 420). In some embodiments, the processing device 140 may encrypt the metadata of the image file to obtain the encrypted metadata. For example, the processing device 140 may encrypt the metadata of the image file using a data encryption algorithm. Exemplary data encryption algorithms may include an advanced encryption standard (AES) algorithm, a Diffie-Hellman algorithm, etc. The processing device 140 may further store the encrypted metadata of the image file.

In 920, the processing device 140 may divide image data of the image file into at least one sub-image data set.

In some embodiments, the processing device 140 may divide the image data of the image file into the at least one sub-image data set based on a file size threshold. More descriptions for the obtaining of at least one sub-image data set may be found elsewhere in the present disclosure (e.g., FIG. 4 and the descriptions thereof).

In 930, the processing device 140 may store, onto a second storage device of at least one second storage device, each sub-image data set of the at least one sub-image data set.

In some embodiments, the processing device 140 may store at least one encoded sub-image data set onto the at least one second storage device (e.g., the at least one image data storage module 440). More descriptions for the storage of the at least one sub-image data set may be found elsewhere in the present disclosure (e.g., FIG. 4 and the descriptions thereof).

In 940, the processing device 140 may store, onto the first storage device, access information of the at least one second storage device.

In some embodiments, the processing device 140 may store the corresponding metadata, an identifier of each of the at least one encoded sub-image data set, and/or the access information of the at least one second storage device onto the first storage device. More descriptions for the storage of the access information of the at least one second storage device may be found elsewhere in the present disclosure (e.g., FIG. 4 and the descriptions thereof).

Figure 10:
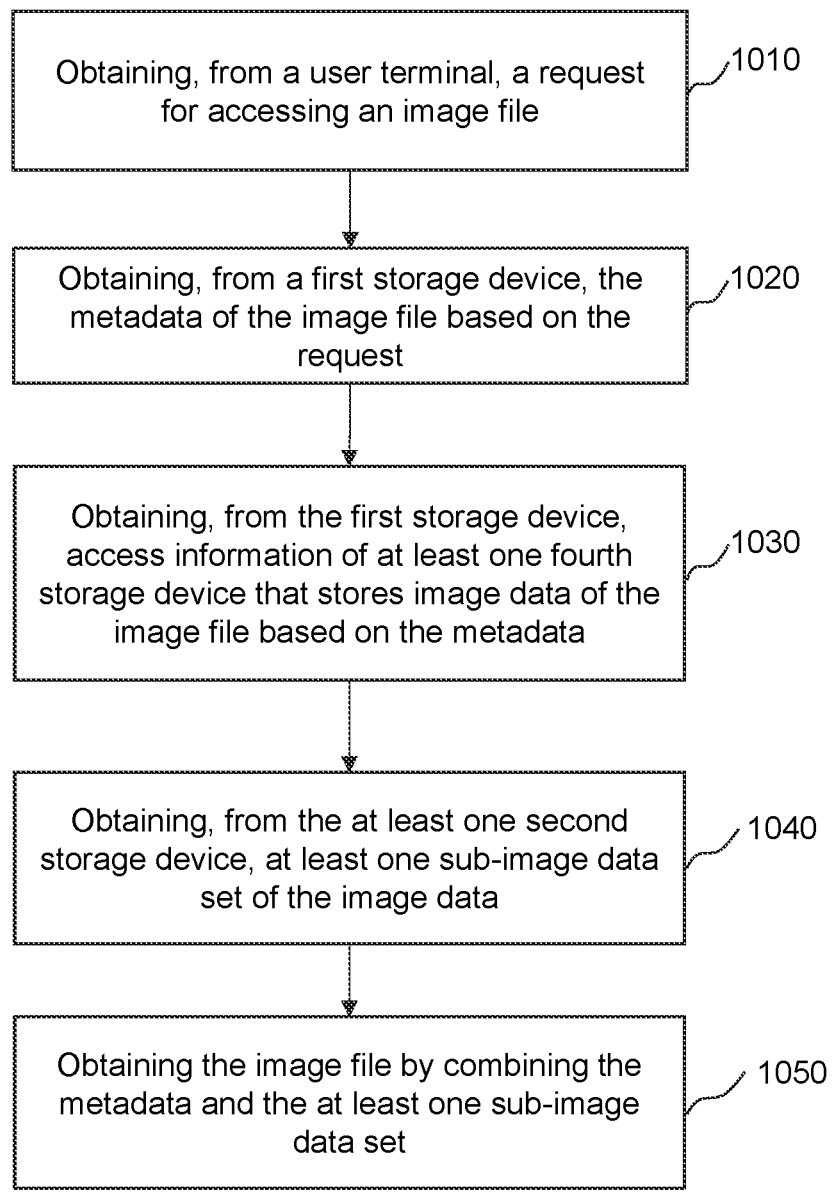
FIG. 10 is a flowchart illustrating an exemplary process for accessing data according to some embodiments of the present disclosure.

FIG. 10 is a flowchart illustrating an exemplary process 1000 for accessing data according to some embodiments of the present disclosure. In some embodiments, the process 1000 may be implemented in the imaging system 100 illustrated in FIG. 1. For example, the process 1000 may be stored in a storage (e.g., the storage device 150, the storage device 220, the storage 390) as a form of instructions, and invoked and/or executed by the processing device 140 (e.g., the processor 210 of the computing device 200 as illustrated in FIG. 2, the CPU 340 of the mobile device 300 as illustrated in FIG. 3, and/or one or more modules as illustrated in FIGS. 4-8). The operations of the illustrated process presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting.

In 1010, the processing device 140 may obtain, from a user terminal (e.g., the terminal 130), a request for accessing an image file (or referred to as a target image file).

In some embodiments, the image file may include metadata and image data. More descriptions for the metadata and image data of the image file may be found elsewhere in the present disclosure (e.g., FIG. 4 and the descriptions thereof).

In 1020, the processing device 140 may obtain, from the first storage device, the metadata of the image file based on the request.

In some embodiments, the processing device 140 may obtain an identifier corresponding to the metadata of the image file by parsing the request. The processing device 140 may further obtain, from the first storage device (e.g., the metadata storage module 420), the metadata of the image file based on the identifier corresponding to the metadata of the image file.

In 1030, the processing device 140 may obtain, from the first storage device, access information of the at least one second storage device that stores image data of the image file based on the metadata.

In 1040, the processing device 140 may obtain, from the at least one second storage device, at least one sub-image data set of the image data.

In some embodiments, the processing device 140 may obtain an identifier of each of the at least one sub-image data set based on the metadata of the target image file. The processing device 140 may further obtain, from the at least one second storage device, the at least one sub-image data set based on the identifier of each of the at least one sub-image data set and the access information of at least one second storage device.

In 1050, the processing device 140 may obtain the image file by combining the metadata and the at least one sub-image data set.

In some embodiments, the processing device 140 may merge the at least one sub-image data set of the image file to generate the image data of the image file. The processing device 140 may combine the image data and the metadata of the image file to obtain the image file. More descriptions for the obtaining of the image file may be found elsewhere in the present disclosure (e.g., FIGS. 7A-7B and the descriptions thereof).

Figure 11:
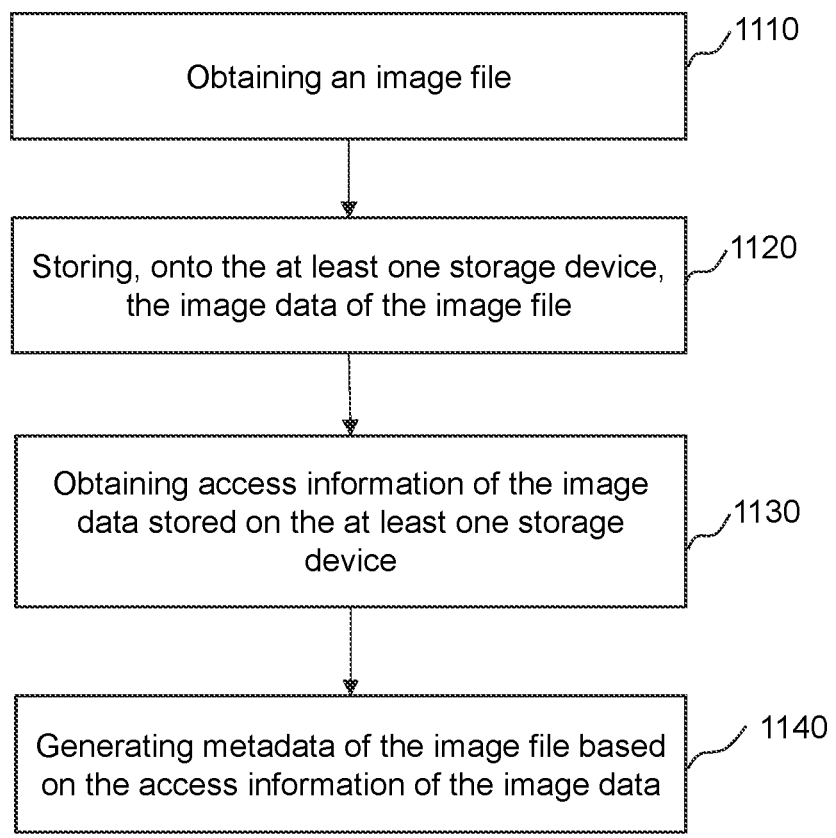
FIG. 11 is a flowchart illustrating an exemplary process for archiving data according to some embodiments of the present disclosure.

FIG. 11 is a flowchart illustrating an exemplary process 1100 for archiving data according to some embodiments of the present disclosure. In some embodiments, the process 1100 may be implemented in the imaging system 100 illustrated in FIG. 1. For example, the process 1100 may be stored in a storage (e.g., the storage device 150, the storage device 220, the storage 390) as a form of instructions, and invoked and/or executed by the processing device 140 (e.g., the processor 210 of the computing device 200 as illustrated in FIG. 2, the CPU 340 of the mobile device 300 as illustrated in FIG. 3, and/or one or more modules as illustrated in FIGS. 4-8). The operations of the illustrated process presented below are intended to be illustrative. In some embodiments, the process 1100 may be accomplished with one or more additional operations not described, and/or without one or more of the operations discussed. Additionally, the order in which the operations of the process 1100 as illustrated in FIG. 11 and described below is not intended to be limiting.

In 1110, the processing device 140 may obtain an image file.

In some embodiments, the processing device 140 may obtain the image file from an imaging device (e.g., the imaging device 110 of the imaging system 100) or an external device (e.g., the terminal 130). In some embodiments, the image file may include metadata and image data of the image file. More descriptions for the metadata and image data of the image file may be found elsewhere in the present disclosure. See, e.g., operation 1210 in FIG. 12 and the descriptions thereof.

In 1120, the processing device 140 may store, onto the at least one storage device, the image data of the image file.

In some embodiments, the processing device 140 may divide the image data of the image file into the at least one sub-image data set and store the at least one sub-image data set. More descriptions for the storage of the image data of the image file may be found elsewhere in the present disclosure (e.g., FIG. 4 and the descriptions thereof).

In 1130, the processing device 140 may obtain access information of the image data stored on the at least one storage device.

After the image data is stored, the processing device 140 may obtain the access information of the image data stored on the at least one storage device.

In 1140, the processing device 140 may generate metadata of the image file based on the access information of the image data.

The processing device 140 may combine the access information of the image data into the metadata of the image file to obtain the combined metadata of the image file. The processing device 140 may store the combined metadata of the image file onto a storage device for storing metadata. More descriptions for the storage of the metadata may be found elsewhere in the present disclosure (e.g., FIG. 4 and the descriptions thereof).

Figure 12:
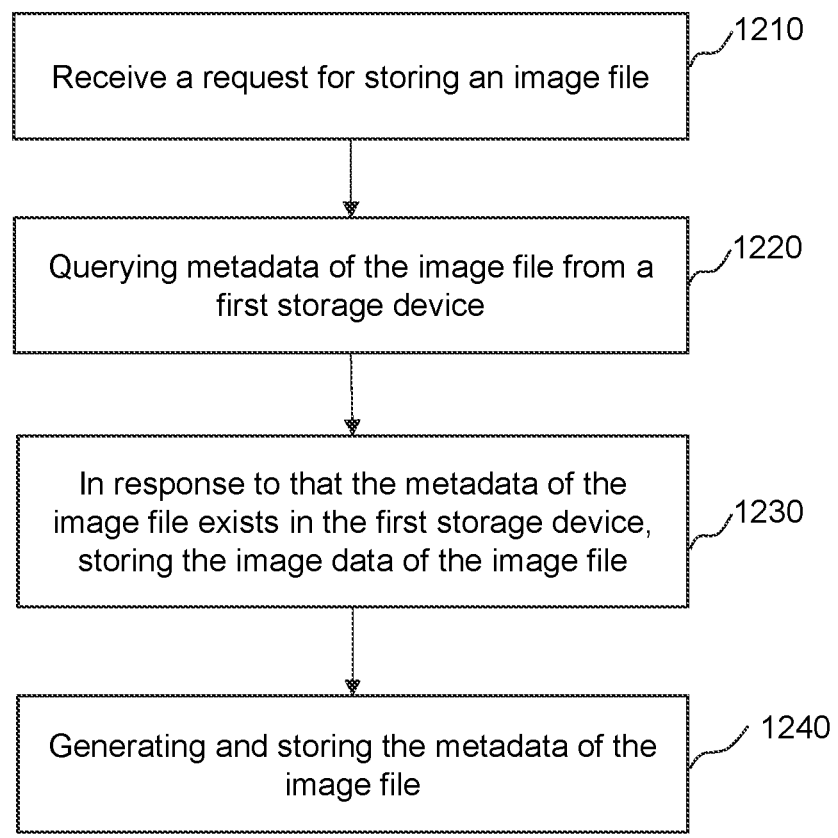
FIG. 12 is a flowchart illustrating an exemplary process for archiving data according to some embodiments of the present disclosure.

FIG. 12 is a flowchart illustrating an exemplary process 1200 for archiving data according to some embodiments of the present disclosure. In some embodiments, the process 1200 may be implemented in the imaging system 100 illustrated in FIG. 1. For example, the process 1200 may be stored in a storage (e.g., the storage device 150, the storage device 220, the storage 390) as a form of instructions, and invoked and/or executed by the processing device 140 (e.g., the processor 210 of the computing device 200 as illustrated in FIG. 2, the CPU 340 of the mobile device 300 as illustrated in FIG. 3, and/or one or more modules as illustrated in FIGS. 4-8). The operations of the illustrated process presented below are intended to be illustrative. In some embodiments, the process 1200 may be accomplished with one or more additional operations not described, and/or without one or more of the operations discussed. Additionally, the order in which the operations of the process 1200 as illustrated in FIG. 12 and described below is not intended to be limiting.

In 1210, the processing device 140 may receive a storage request for storing an image file.

In some embodiments, the processing device 140 may obtain the image file from an imaging device (e.g., the imaging device 110 of the imaging system 100) or an external device (e.g., a terminal 130). In some embodiments, the image file may include metadata and image data of the image file. The metadata of the image file refers to data for describing the image file. Exemplary metadata may include a name of the image file, a storage ID of the image file, a length of the image file, a timestamp of the image file, a service-object pair (SOP) class unique identifier (UID), an SOP instance UID, a study instance UID, a series instance UID, a patient ID, a patient name, a date of birth of a patient, a description of illness of a patient, or the like, or any combination thereof. The study instance UID may include identifiers of a plurality of examinations for a patient. The metadata of the image file may be recorded in a Table 1 below.

TABLE 1

Metadata Record

| Field Name | Type | Length | Description |
| --- | --- | --- | --- |
| name | string | 128 | Unique identifier of the image file |
| id | string | 32 | Storage ID of the image file |
| len | long | | Length of the image file (bytes) |
| time | date | | Timestamp of the image file |
| SOP_Class_UID | string | 512 | Service-object pair (SOP) class unique identifier (UID) |
| SOP_Instance_UID | string | 512 | SOP instance UID |
| Patient_ID | string | 64 | Identifier of a subject corresponding to the image file |
| Patient_Name | string | 64 | Name of a subject corresponding to the image file |
| Study_Instance_UID | string | 512 | Identifier of an examination corresponding to the image file |
| Series_Instance_UID | string | 512 | Series instance UID |

More descriptions for the metadata and image data of the image file may be found elsewhere in the present disclosure (e.g., FIG. 4 and the descriptions thereof).

In 1220, the processing device 140 may query metadata of the image file from a first storage device (e.g., by searching the metadata of the image file in a metadata record table stored in the first storage device).

In some embodiments, the first storage device may be configured to enable real-time query. For example, the first storage device may include at least one of Apache Kudu, Elasticsearch, HBase, or the like. More descriptions for the querying of the metadata of the image file may be found elsewhere in the present disclosure (e.g., FIG. 13 and the descriptions thereof).

If the metadata of the image file exists in the first storage device (or the metadata record table), the image file has been stored. The processing device 140 may send a message indicating that the image file has been stored to a user terminal that sends the request. If the metadata of the image file does not exist in the first storage device (or the metadata record table), the image file is not stored in the first storage device. The processing device 140 may perform operations 1230 and 1240.

In 1230, in response to that the metadata of the image file does not exist in the first storage device (or the metadata record table), the processing device 140 may store the image data of the image file.

The storage request may include address information of a plurality of second storage devices that are used to store the image data of the image file. The processing device 140 may store the image data of the image file onto at least one of the plurality of second storage devices based on the address information of the plurality of second storage devices. In some embodiments, the processing device 140 may divide the image data (or compressed image data) of the image file into the at least one sub-image data set and store the at least one sub-image data set. More descriptions for the storage of the image data of the image file may be found elsewhere in the present disclosure (e.g., FIGS. 4-5 and the descriptions thereof).

In 1240, the processing device 140 may generate and/or store the metadata of the image file.

In some embodiments, after the image data of the image file is stored, the processing device 140 may obtain access information of the image data stored on the at least one second storage device. As used herein, the access information may be information that describes the image file. For example, the access information may include the address information of the at least one second storage device, an identifier of the image data, or the like, or any combination thereof. The processing device 140 may combine the access information of the image data into the metadata of the image file to obtain the combined metadata of the image file. The processing device 140 may store the combined metadata of the image file onto the first storage device. For example, the processing device 140 may insert the access information into the metadata record table (e.g., Table 1) and generate the combined metadata of the image file. The processing device 140 may further store the combined metadate into the first storage device.

According to some embodiments of the present disclosure, the combined metadata of the image file may be stored onto the first storage device configured to enable real-time query. When the image file is subsequently retrieved, the metadata of the image file may be searched in real-time, which may improve the efficiency and/or reliability of obtaining of the image file. In addition, the metadata is correlated with the image file, which may have a high maintainability.

Figure 13:
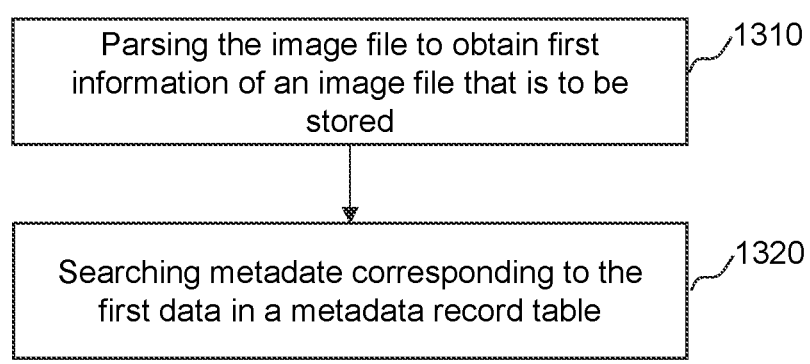
FIG. 13 is a flowchart illustrating an exemplary process for querying metadata of an image file according to some embodiments of the present disclosure.

FIG. 13 is a flowchart illustrating an exemplary process 1300 for querying metadata of an image file according to some embodiments of the present disclosure. In some embodiments, one or more operations of the process 1300 may be performed to achieve at least part of operation 1220 as described in connection with FIG. 12.

In 1310, the processing device 140 may parse the image file to obtain first information of an image file that is to be stored.

In some embodiments, a terminal (e.g., the terminal 130) may send an image file to be stored to the processing device 140. The processing device 140 may parse the image file to obtain the first information of the image file.

In some embodiments, the first information may include information describing the image file. For example, the processing device 140 may obtain information relating to the image file, and designated the information relating to the image file as the first information. For example, the information relating to the image file (or the first information) may include a service-object pair (SOP) class unique identifier (UID), an SOP instance UID, a study instance UID, a series instance UID, a patient ID, a patient name, a name of the image file, a length of the image file, a storage ID of the image file, a timestamp of the image file, or the like, or any combination thereof.

In 1320, the processing device 140 may search metadate corresponding to the first information in a metadata record table.

In some embodiments, the processing device 140 may query or search the metadate corresponding to the first information in the metadata record table that is stored in the first storage device. For example, the processing device 140 may query or search the name of the image file. As another example, the processing device 140 may query or search the SOP instance UID.

If the metadata of the image file exists in the first storage device, the image file has been archived. The processing device 140 may send, to a user terminal, a message indicating that the image file has been archived. If the metadata of the image file does not exist in the first storage device, the image file is not archived yet.

According to the process 1200 and process 1300, the metadata may be searched in real time according to the first information relating to the image file. In this way, accessing image files (or the metadata or the image data thereof) in real-time without accessing index information of the image files may effectively improve efficiency and/or reliability of storage and reduce costs of management and maintenance.

Figure 14:
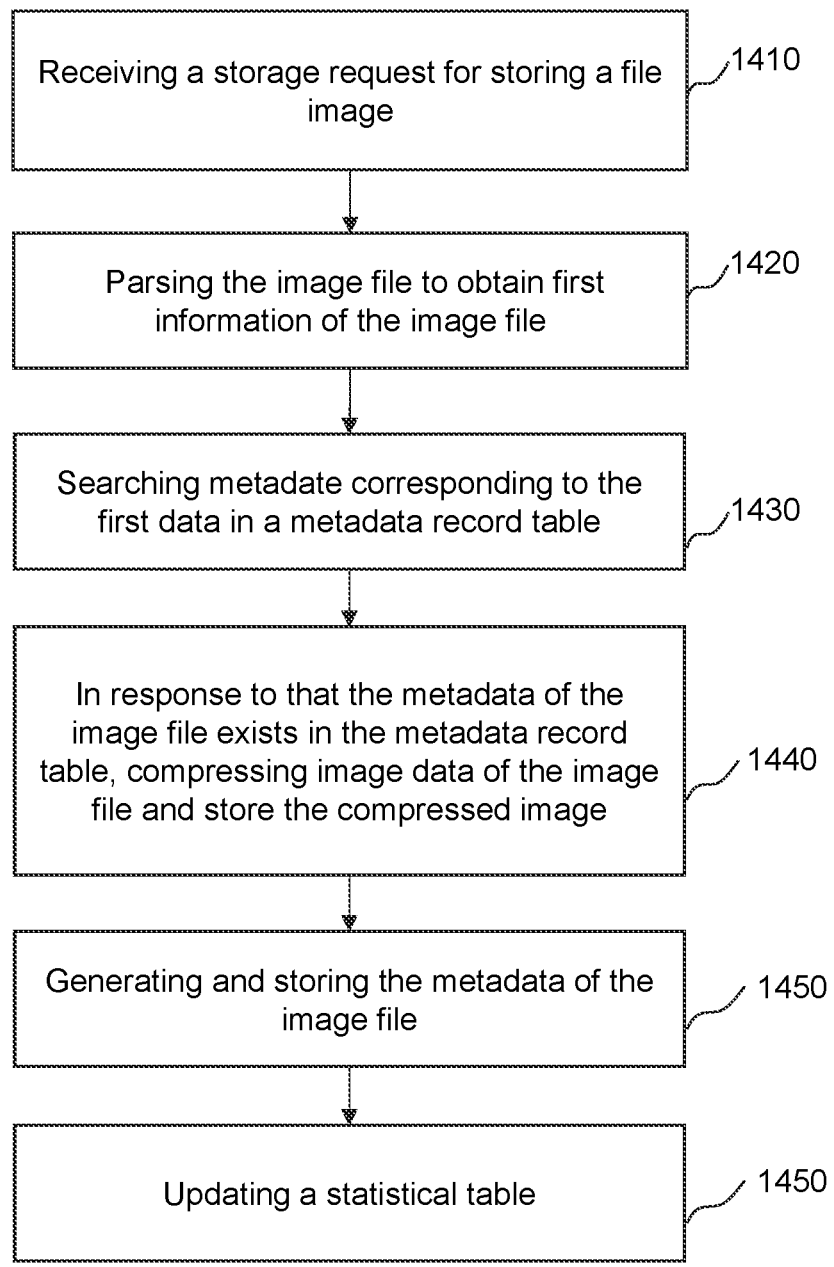
FIG. 14 is a flowchart illustrating an exemplary process for archiving data according to some embodiments of the present disclosure.

FIG. 14 is a flowchart illustrating an exemplary process 1400 for archiving data according to some embodiments of the present disclosure. In some embodiments, the process 1400 may be implemented in the imaging system 100 illustrated in FIG. 1. For example, the process 1400 may be stored in a storage (e.g., the storage device 150, the storage device 220, the storage 390) as a form of instructions, and invoked and/or executed by the processing device 140 (e.g., the processor 210 of the computing device 200 as illustrated in FIG. 2, the CPU 340 of the mobile device 300 as illustrated in FIG. 3, and/or one or more modules as illustrated in FIGS. 4-8). The operations of the illustrated process presented below are intended to be illustrative. In some embodiments, the process 1400 may be accomplished with one or more additional operations not described, and/or without one or more of the operations discussed. Additionally, the order in which the operations of the process 1400 as illustrated in FIG. 14 and described below is not intended to be limiting.

In 1410, the processing device 140 may receive a storage request for storing an image file. The operation 1410 may be similar to or the same as the operation 1210 of the process 1200 as illustrated in FIG. 12.

In 1420, the processing device 140 may parse the image file to obtain the metadata of the image file to be stored. The operation 1420 may be similar to or the same as the operation 1310 of the process 1300 as illustrated in FIG. 13.

In 1430, the processing device 140 may search metadate corresponding to the first information in a metadata record table. The operation 1430 may be similar to or the same as the operation 1320 of the process 1300 as illustrated in FIG. 13.

In 1440, in response to that the metadata of the image file does not exist in the metadata record table, the processing device 140 may compress the image data of the image file and store the compressed image data of the image file. The operation 1440 may be similar to or the same as the operation 1230 of the process 1200 as illustrated in FIG. 13.

In some embodiments, in response to that the metadata of the image file does not exist in the metadata record table, the processing device 140 may compress the image data of the image file using a compression algorithm for DICOM file. Exemplary compression algorithms may include JPEG Lossless algorithm. The processing device 140 may further store the compressed image data of the image file, which may reduce storage space.

In 1450, the processing device 140 may generate and store the metadata of the image file. The operation 1450 may be similar to or the same as the operation 1240 of the process 1200 as illustrated in FIG. 13.

In 1460, the processing device 140 may update a statistical table.

The statistical table may be configured to record a file count of image data in the at least one second storage device, an occupied storage space of the at least one second storage device, a frequency count by which the metadata or the image data of the image file are accessed, or the like, or any combination thereof. In some embodiments, after the image data of the image file is stored onto the at least one second storage device, the processing device 140 may determine a file count of image data in each of the at least one storage device or an occupied storage space of each of the at least one second storage device. The processing device 140 may determine the file count of image data in the at least one storage device or the occupied storage space of the at least one second storage device based on the file count of image data in each of the at least one storage device or an occupied storage space of each of the at least one second storage device. The processing device 140 may update the statistical table after the file count of image data in the at least one storage device or an occupied storage space of the at least one second storage device are determined.

In some embodiments, the processing device 140 may determine a free storage space of each of the at least one second storage device, and the free storage space of a parent directory of the at least one second storage device. If the free storage space of one of the at least one second storage device is less than a first storage threshold or the free storage space of the parent directory is less than a second storage threshold, the processing device 140 may send a prompt message to a terminal (e.g., the imaging device 110, the terminal 130). In this way, the occupied storage space and/or the free storage space of the at least one second storage device (and/or the parent directory) may be monitored in real-time to facilitate the management of the storage of the image data.

Figure 15:
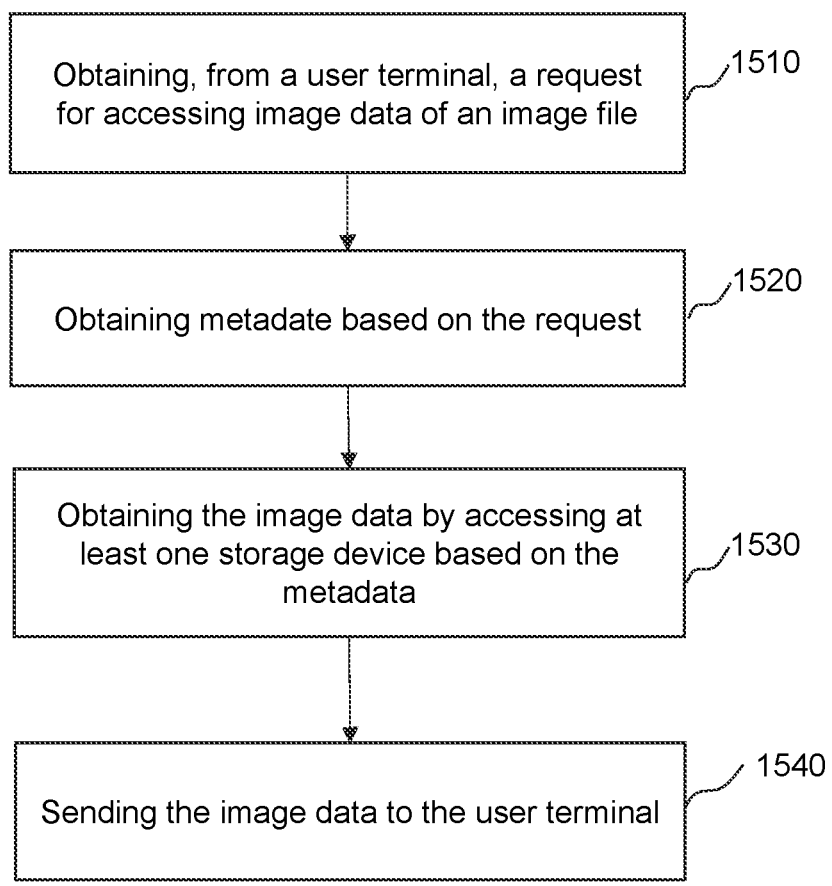
FIG. 15 is a flowchart illustrating an exemplary process for accessing data according to some embodiments of the present disclosure.

FIG. 15 is a flowchart illustrating an exemplary process 1500 for archiving data according to some embodiments of the present disclosure. In some embodiments, the process 1500 may be implemented in the imaging system 100 illustrated in FIG. 1. For example, the process 1500 may be stored in a storage (e.g., the storage device 150, the storage device 220, the storage 390) as a form of instructions, and invoked and/or executed by the processing device 140 (e.g., the processor 210 of the computing device 200 as illustrated in FIG. 2, the CPU 340 of the mobile device 300 as illustrated in FIG. 3, and/or one or more modules as illustrated in FIGS. 4-8). The operations of the illustrated process presented below are intended to be illustrative. In some embodiments, the process 1500 may be accomplished with one or more additional operations not described, and/or without one or more of the operations discussed. Additionally, the order in which the operations of the process 1500 as illustrated in FIG. 15 and described below is not intended to be limiting.

In 1510, the processing device 140 may obtain, from a user terminal, a request for accessing image data of an image file.

The request for accessing image data of an image file may include information for retrieving metadata. Exemplary information for retrieving the metadata may include a service-object pair (SOP) class unique identifier (UID), an SOP instance UID, a study instance UID, a series instance UID, a patient ID, a patient name, a name of the image file, a length of the image file, a storage ID of the image file, a timestamp of the image file, a type (e.g., a PET file, a CT image file, etc.) of the image file, or the like, or any combination thereof.

In some embodiments, a user may input the information for retrieving metadata via a user terminal (e.g., the terminal 130). The user terminal may generate the request for accessing the image data based on the information for retrieving metadata input by the user, and send the request for accessing image data of an image file to the processing device 140. For example, the user may input a patient name and/or an SOP instance UID via the user terminal. The user terminal may generate the request including the patient name and the SOP instance UID, and send the request to the processing device 140.

In 1520, the processing device 140 may obtain metadata of the image data based on the request.

In some embodiments, the processing device 140 may query the metadata of the image file from a storage device (e.g., the first storage device, the metadata storage module 420) by searching the metadata of the image file in a metadata record table stored in the storage device based on the information for retrieving metadata. For example, the processing device 140 may query the metadata of the image file in the metadata record table using the patient name and/or the SOP instance UID.

If the metadata of the image file exists in the storage device or the metadata record table, the processing device 140 may perform operation 1530. If the metadata of the image file does not exist in the storage device or the metadata record table, the processing device 140 may send a message indicating that the metadata of the image file does not exist to the user terminal.

In 1530, the processing device 140 may obtain the image data by accessing at least one storage device for storing the image data based on the metadata.

In response that the metadata of the image file exists in the storage device or the metadata record table, the processing device 140 may obtain, from the metadata, accessing information of the at least one storage device that stores the image data. The processing device 140 may obtain the image data by accessing the at least one storage device based on the accessing information of the at least one storage device.

In some embodiments, the processing device 140 may obtain a frequency count by which the metadata or the image data of the image file are accessed. The frequency count may be a total count of times of the metadata or the image data of the image file have been accessed by user terminals. The frequency count may be stored in a preset statistical table. After the metadata of the image file is obtained, the processing device 140 may obtain the frequency count from the preset statistical table. The processing device 140 may determine whether the metadata or the image data is frequently accessed based on the frequency count. For example, if the frequency count exceeds a frequency threshold, the processing device 140 may determine that the metadata or the image data is frequently accessed.

In response to determining that the metadata or the image data is frequently accessed, the processing device 140 may obtain the image data from a buffer. The buffer may store the image data. In response to determining that the metadata or the image data is not frequently accessed, the processing device 140 may obtain the image data directly from the at least one storage device. In some embodiments, after the image data is obtained, the processing device 140 may store the image data into the buffer. In some embodiments, after the image data is obtained, the processing device 140 may update the frequency count. The access efficiency and/or reliability of image data may be improved by storing the image data into the buffer.

In 1540, the processing device 140 may send the image data to the user terminal. In some embodiments, the processing device 140 may combine the image data and the metadata of the image data (or the image file) to obtain the image file, and send to the user terminal. In some embodiments, the processing device 140 may send, to the user terminal, the image data and/or the metadata of the image data (or the image file) separately.

When an image file is stored by a conventional data storage method, metadata of the image file only includes information relating to the image file. Information relating to the image data of the image file and index information of the image file are stored in an index database. A server often obtains the information relating to the image file according to the index information. Further, the server may obtain the image data according to the information relating to the image file. However, according to some embodiments of the process 1500, the metadata may include information relating to the image file and information relating to the image data of the image file. The processing device 140 may obtain the image data according to the metadata directly. The efficiency and/or reliability of accessing the image data may be improved.

Figure 16:
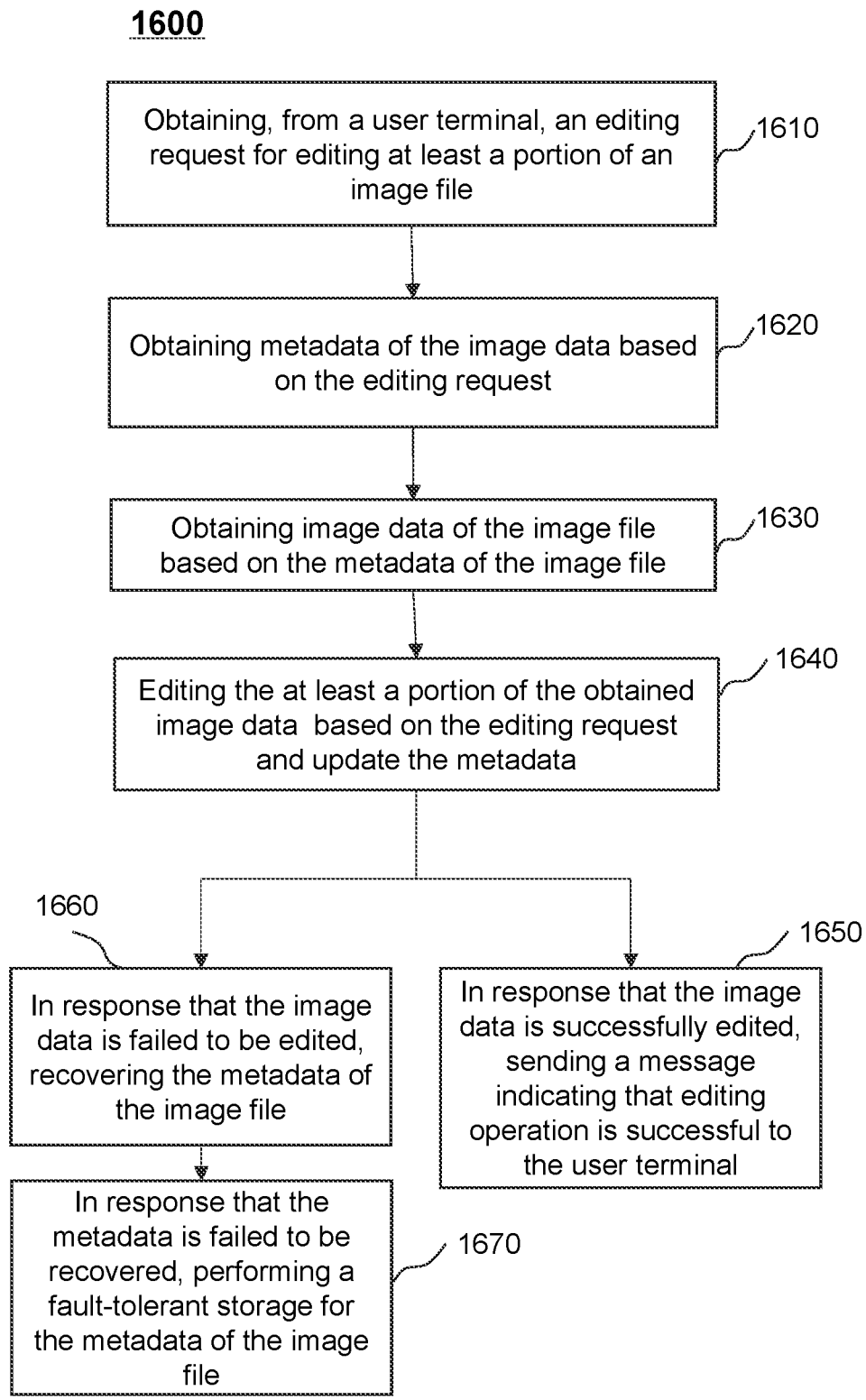
FIG. 16 is a flowchart illustrating an exemplary process for editing data according to some embodiments of the present disclosure.

FIG. 16 is a flowchart illustrating an exemplary process 1600 for editing data according to some embodiments of the present disclosure. In some embodiments, the process 1600 may be implemented in the imaging system 100 illustrated in FIG. 1. For example, the process 1600 may be stored in a storage (e.g., the storage device 150, the storage device 220, the storage 390) as a form of instructions, and invoked and/or executed by the processing device 140 (e.g., the processor 210 of the computing device 200 as illustrated in FIG. 2, the CPU 340 of the mobile device 300 as illustrated in FIG. 3, and/or one or more modules as illustrated in FIGS. 4-8). The operations of the illustrated process presented below are intended to be illustrative. In some embodiments, the process 1600 may be accomplished with one or more additional operations not described, and/or without one or more of the operations discussed. Additionally, the order in which the operations of the process 1600 as illustrated in FIG. 16 and described below is not intended to be limiting.

In 1610, the processing device 140 may obtain, from a user terminal, an editing request for editing at least a portion of an image file.

In some embodiments, the editing request may include modifying, updating, or deleting the at least a portion of the image file (e.g., the metadata, the image data or a portion thereof).

In some embodiments, the editing request may include information for retrieving metadata. More descriptions for the information for retrieving metadata may be found elsewhere in the present disclosure. See, e.g., operation 1510 in FIG. 15 and the descriptions thereof. In some embodiments, a user may input the information for retrieving metadata via the user terminal. The user terminal may generate the editing request based on the information for retrieving metadata input by the user, and send the editing request to the processing device 140. The processing device 140 may parse the editing request to obtain the information for retrieving metadata.

In 1620, the processing device 140 may obtain metadata of the image data based on the editing request.

In some embodiments, the processing device 140 may query metadata of the image data from a storage device (e.g., the first storage device, the metadata storage module 420) by searching the metadata of the image file in a metadata record table stored in the storage device based on the information for retrieving metadata. For example, if the information for retrieving metadata include an SOP instance UID, the processing device 140 may query the SOP instance UID from the storage device or the metadata record table.

If the information for retrieving metadata exists in the storage device or the metadata record table, the processing device 140 may determine the metadata of the image data from the storage device for storing the metadata, and perform operation 1630. If the information for retrieving metadata does not exist, the processing device 140 may send a message indicating a failure editing to the user terminal.

In 1630, the processing device 140 may obtain image data of the image file based on the metadata of the image file.

In some embodiments, the processing device 140 may obtain, from the metadata of the image file, a name of the image file and accessing information of at least one storage device (e.g., the at least one second storage device, the at least one image data storage module 440) that the image data of the image file. In some embodiments, the processing device 140 may further obtain the image data of the image file by accessing the at least one storage device based on the access information. In some embodiments, the processing device 140 may obtain address information of the at least one storage device.

In 1640, the processing device 140 may edit the at least a portion of the obtained image data based on the editing request and update the metadata.

In some embodiments, the editing request may include new information for replacing or modifying the at least a portion of the obtained image data. The processing device 140 may replace or modify the at least a portion of the obtained image data with the new information based on the editing request. After replacing or modifying the image data, the processing device 140 may update the metadata based on the replaced or modified image data. In some embodiments, the processing device 140 may delete the at least a portion of the obtained image data based on the editing request. The processing device 140 may delete the metadata of the deleted image data.

In some embodiments, the processing device 140 may determine whether the editing operation is successful. In response to determining that the editing operation is successful, operation 1650 may be performed. In response to determining that the editing operation is not successful, operation 1660 may be performed.

In 1650, in response that the image data is successfully edited, the processing device 140 may send a message indicating that the editing operation is successful to the user terminal.

In some embodiments, if editing operation is a modifying operation, the processing device 140 may send a message indicating that modifying operation is successful to the user terminal. The processing device 140 may further send the modified image data or the metadata to the user terminal.

In some embodiments, if the editing operation is a deleting operation, the processing device 140 may send a message indicating that deleting operation is successful to the user terminal.

In 1660, the processing device 140 may recover the metadata of the image file.

In some embodiments, the processing device 140 may send a message indicating that the modifying operation or the deleting operation is not successful to the user terminal. The processing device 140 may further recover the metadata to the original metadata of the image file before the modifying operation is performed.

In some embodiments, the processing device 140 may determine whether the recovery of the metadata of the image file is successful. In response to determining that the recovery of the metadata of the image file is successful, the processing device 140 may send a message indicating that the recovery of the metadata of the image file is successful to the user terminal. In response to determining that the recovery of the metadata of the image file is not successful, operation 1670 may be performed.

In 1670, the processing device 140 may perform a fault-tolerant storage for the metadata of the image file.

In some embodiments, if editing operation is a modifying operation, the processing device 140 may store the original metadata before the modifying operation is performed onto a fault-tolerant storage device. In some embodiments, if editing operation is a deleting operation, the processing device 140 may store the deleted metadata onto the fault-tolerant storage device.

If the recovery of the metadata of the image file is not successful, the metadata in the storage device (e.g., the first storage device) is no longer corresponding to the image data of the image file. In this case, the fault-tolerant storage for the metadata of the image file may be performed. When the image data being edited next time, the image data may be determined according to the metadata stored in the fault-tolerant storage device to perform further editing operation for the image data.

Figure 17:
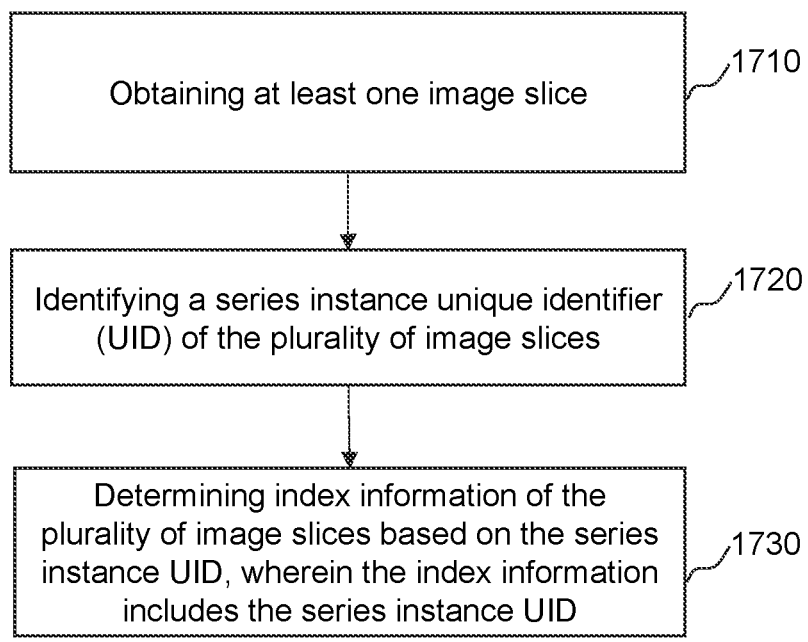
FIG. 17 is a flowchart illustrating an exemplary process for determining index information of an image sequence according to some embodiments of the present disclosure.

FIG. 17 is a flowchart illustrating an exemplary process 1700 for determining index information of an image sequence according to some embodiments of the present disclosure. In some embodiments, the process 1700 may be implemented in the imaging system 100 illustrated in FIG. 1. For example, the process 1700 may be stored in a storage (e.g., the storage device 150, the storage device 220, the storage 390) as a form of instructions, and invoked and/or executed by the processing device 140 (e.g., the processor 210 of the computing device 200 as illustrated in FIG. 2, the CPU 340 of the mobile device 300 as illustrated in FIG. 3, and/or one or more modules as illustrated in FIGS. 4-8). The operations of the illustrated process presented below are intended to be illustrative. In some embodiments, the process 1700 may be accomplished with one or more additional operations not described, and/or without one or more of the operations discussed. Additionally, the order in which the operations of the process 1700 as illustrated in FIG. 17 and described below is not intended to be limiting.

In 1710, the processing device 140 may obtain at least one image slice of the image sequence. The image sequence may refer to at least one image (or referred to as an image slice) of a subject obtained by a same imaging device (e.g., the imaging device 110 described in FIG. 1) in a same examination. The at least one image (or referred to as an image slice) may be associated with each other using hash values according to a hash algorithm. In some embodiments, the at least one image slice may be ordered according to their respective acquisition time points during the medical examination. For example, an image slice that is obtained earliest among the at least one image slice may be a lead image slice, and an image that is obtained latest among the at least one image slice may be a last image slice of the at least one image slice. In some embodiments, the at least one image slice may be obtained by performing an examination on different position of the subject at a same time. An image slice of a first position of the subject may be a lead image slice, and an image slice of a last position of the subject may be a last image slice.

In some embodiments, the processing device 140 may obtain the at least one image slice from an imaging device (e.g., the imaging device 110 of the imaging system 100) or an external device (e.g., the terminal 130). More descriptions for the obtaining of the at least one image slice may be found elsewhere in the present disclosure (e.g., FIG. 4, FIG. 18, and the descriptions thereof).

In 1720, the processing device 140 may identify a series instance unique identifier (UID) of the image series. More descriptions for the series UID may be found elsewhere in the present disclosure (e.g., FIG. 18, and the descriptions thereof).

In 1730, the processing device 140 may determine index information of the image sequence based on the series instance UID. In some embodiments, the index information of the image sequence may include index information of a lead image slice of the at least one image slice. The index information of the lead image slice may include the series instance UID, a storage ID of a storage device that stores the lead image slice, a hash value of a last image slice of the at least one image slice, or the like, or any combination thereof.

In some embodiments, the processing device 140 may identify the series instance UID by parsing any one image slice of the image sequence. For example, each of the at least one image slice may be labeled with the series instance UID. After the at least one image slice is stored, the storage ID of the storage device that stores the lead image slice may be obtained. In some embodiments, the processing device 140 may determine a hash value for each image slice of the at least one image slice according to a Hash algorithm. For example, a hash value of a first image slice which is immediately next to a second image slice of the plurality of image slices may be determined based on a hash value of the second image slice according to the hash algorithm. A hash value of the lead image slice may be designated as the series instance UID. For example, the at least one image slice includes two images. The processing device 140 may designate a hash value of the lead image slice of the two images as the series instance UID. The processing device 140 may determine a hash value of an image slice (a last image of the two images) which is immediately next to the lead image slice based on the series instance UID, and designated the determined hash value as the hash value of the last image of the two images. As another example, the at least one image slice includes three images. The processing device 140 may designate a hash value of the lead image slice of the three images as the series instance UID. The processing device 140 may determine a hash value of an image slice (a second image of the three images) which is immediately next to the lead image slice based on the series instance UID, and further determine a hash value of another image slice (a third image of the three images) which is immediately next to the image slice (the second image) based on the hash value of the image slice (the second image of the three images). The processing device 140 may designate the determined hash value of the other image slice (the third image of the three images) as the hash value of the last image of the three images. The hash value of the last image of the at least one image slice may be part of the index information of the image sequence and stored in an index table. More descriptions for the index information of the image sequence may be found elsewhere in the present disclosure (e.g., FIG. 18, FIG. 19, FIG. 21, and the descriptions thereof).

Figure 18:
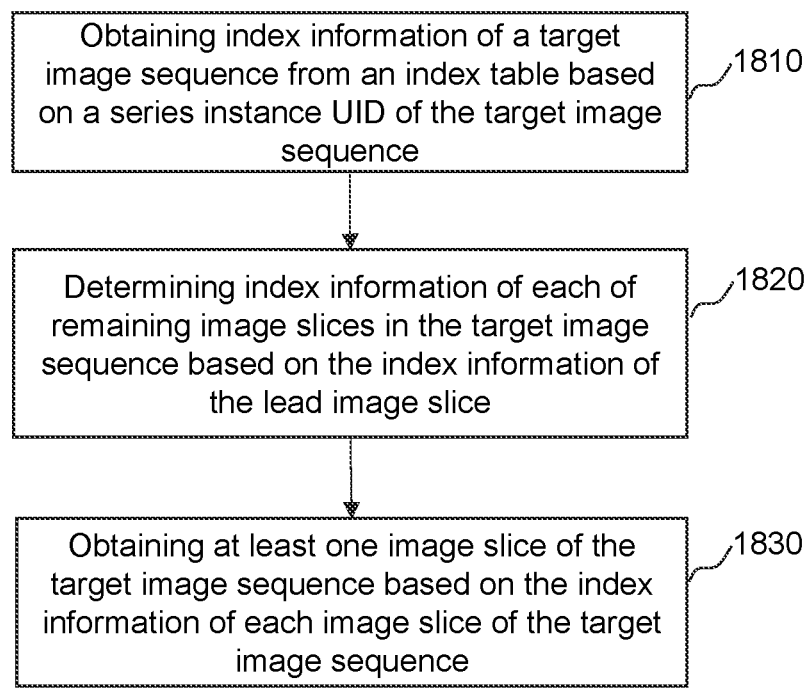
FIG. 18 is a flowchart illustrating an exemplary process for accessing data according to some embodiments of the present disclosure.

FIG. 18 is a flowchart illustrating an exemplary process 1800 for accessing data according to some embodiments of the present disclosure. In some embodiments, the process 1800 may be implemented in the imaging system 100 illustrated in FIG. 1. For example, the process 1800 may be stored in a storage (e.g., the storage device 150, the storage device 220, the storage 390) as a form of instructions, and invoked and/or executed by the processing device 140 (e.g., the processor 210 of the computing device 200 as illustrated in FIG. 2, the CPU 340 of the mobile device 300 as illustrated in FIG. 3, and/or one or more modules as illustrated in FIGS. 4-8). The operations of the illustrated process presented below are intended to be illustrative. In some embodiments, the process 1800 may be accomplished with one or more additional operations not described, and/or without one or more of the operations discussed. Additionally, the order in which the operations of the process 1800 as illustrated in FIG. 18 and described below is not intended to be limiting.

In 1810, the processing device 140 may obtain index information of a target image sequence from an index table based on a series instance UID of a target image sequence.

In some embodiments, the target image sequence refers to an image sequence to be queried or accessed. The target image sequence may include at least one image slice, such as 200 image slices. In some embodiments, one or more medical examinations may be performed for a subject. Each of one or more medical examinations may be performed for one or more portions of the subject. Each of one or more medical examinations may generate an image sequence including at least one image slice. At least one image slice of an image sequence refers to at least one image of a subject obtained by a same imaging device (e.g., the imaging device 110 described in FIG. 1) in a same medical examination. For example, the series instance UID of the target image sequence may be represented as "SeriesUID: 0020, 000E". The series instance UIDs of different image sequences may be different. Therefore, images of different image sequences may be distinguished according to the different series instance UIDs.

In some embodiments, the index table may be a data table established in a database (e.g., a storage device, the first storage device, the metadata storage module 420). The index table may be configured to store index information of multiple image sequences that has been stored. That is, after at least one image slice of an image sequence is stored, the index information of the image sequence may be stored in the index table. The processing device 140 may obtain the index information of the image sequence based on the series instance UID of the image sequence from the index table.

In some embodiments, the index information of the target image sequence may include index information of a lead image slice of the target image sequence. The lead image slice of the target image sequence refers to the first stored image in target image sequence or the first obtained image during an examination. It should be noted that the first stored image and the latest stored image in the subsequent embodiments are only used to distinguish an order of the storage of the at least one image slice of the target image sequence, not to limit other information.

In some embodiments, the index information of an image slice may refer to an ID of image file of the image slice (i.e., a name of image file of the image slice) or an ID of the image slice. Meanings of index information generated using different storage manners are different. For example, if an image slice is stored using a network attached storage (NAS), the index information of the image slice may refer to an ID of the image slice (i.e., a name of the image slice). As another example, if an image slice is stored using an object storage service (OSS), the index information of the image slice may refer to an ID of an image file of the image slice.

In some embodiments, the index information of the lead image slice of the target image sequence may be the series instance UID of the target image sequence. For example, if the series instance UID of the target image sequence is 0020, 000E, the index information of the lead image slice may be 0020, 000E.

In some embodiments, the index information of the lead image slice may be represented as an identifier composed of numbers, letters, or a combination of numbers and letters, which is determined based on storage information. The storage information may include storage time, user information, patient information, examination information, or the like, or any combination thereof.

If the index information of the target image sequence does not exist in the index table, the target image sequence is not stored. If the index information of the target image sequence exists in the index table, the target image sequence has been stored, and the index information of the target image sequence includes index information of the lead image slice.

In 1820, the processing device 140 may determine index information of each of the remaining image slices in the target image sequence based on the index information of the lead image slice.

In some embodiments, before the process 1800 for accessing at least one image slice of the target image sequence, the at least one image slice of the target image sequence may be stored onto a plurality of storage device (e.g., a picture archiving and communication system (PACS), a cloud server, etc.). The processing device 140 may generate an index information determining rule using the index information of each of the at least one image slice of the target image sequence. In some embodiments, the processing device 140 may generate the index information determining rule according to a preset algorithm (e.g., a hash algorithm). For example, the index information (e.g., an ID of an image file of each image slice or an ID of each image slice) of the at least one image slice of the target image sequence may be connected to form a hash chain according to a hash algorithm. After the index information determining rule is generated, the processing device 140 may need to store only the index information of the lead image slice. In this way, only the index information of the lead image slice of the target image sequence is stored when the target image sequence is stored, instead of storing the index information of each image slice. In this way, as occupied storage space of the index information of the target image sequence is reduced, thereby improving the efficiency and/or reliability for archiving and/or retrieval of medical images.

In some embodiments, the index information determining rule may include that the index information of each of the remaining image slices of the target image sequence is generated based on the index information of the lead image slice. For example, if the index information of the lead image slice is Index(1st) and a hash value of the Index(1st) is Hash, the index information of the Nth image slice of the target image sequence may be Hash+(N−1). Where N denotes the storage order of the at least one image slice. For example, the index information of the second image slice may be Hash+1, the index information of the third image slice may be Hash+2, and the index information of the Nth image slice of the target image sequence may be Hash+(N−1). In some embodiments, the processing device 140 may determine the index information of each of the remaining image slices of the target image sequence based on the index information of the lead image slice according to a preset algorithm (e.g., a hash algorithm).

In some embodiments, the index information determining rule may include that index information of each of the remaining image slices of the target image sequence is generated based on index information of an immediately preceding image slice of the image slice. For example, if the index information of the lead image slice is Index(1st), the index information Index(2nd) of the second image slice may be a hash value of the Index(1st), the index information Index(3rd) of the third image slice may be a hash value of the Index(2nd), and the index information Index(N) of the Nth image slice of the target image sequence may be a hash value of the Index(N−1).

In some embodiments, the processing device 140 may determine the index information of the image slice of the target image sequence based on index information of an immediately preceding image slice which is immediately next to the image slice according to a preset algorithm (e.g., a hash algorithm). Merely by way of example, for each image slice of the at least one image slice, the processing device 140 may determine a hash value according to a hash algorithm. A hash value of a first image slice which is immediately next to a second image slice of the at least one image slice may be determined based on a hash value of the second image slice according to a hash algorithm. The processing device 140 may perform a hash operation on the index information of the lead image slice to obtain a hash value of the lead image slice, and designate the hash value of the lead image slice as index information of an image slice which is immediately next to the lead image slice (or a second image of the at least one image slice). The processing device 140 may perform a hash operation on the index information of the lead image slice to obtain a hash value of the second image, and designate the hash value of the second image as index information of an image slice which is immediately next to the second image (or a third image of the at least one image slice). The processing device 140 may perform a hash operation on the index information of the third image to obtain a hash value of the third image, and designate the hash value of the third image as index information of an image slice which is immediately next to the third image (or a fourth image). The obtaining of the index information of each of the remaining image slices may be performed in a similar manner as that of the index information of the second image or the third image. It should be noted that the hash algorithm is only for illustration, other encoding algorithms may also be used to determine the index information of a first image slice which is immediately next to a second image slice of the plurality of image slices based on index information of the second image slice.

In some embodiments, the processing device 140 may determine whether the index information of each image slice has been obtained based on the index information of the last image slice or an amount of the at least one image slice. In some embodiments, if the index information of the target image sequence includes the index information of the last image slice, when the obtained index information of an image slice is the same as the index information of the last image slice, the processing device 140 may determine the index information of each image slice has been obtained. For example, if index information of the target image sequence stored in the index table includes the index information SeriesUID of the lead image slice and the index information hash(n) of the last image slice, the processing device 140 may determine the index information of each image slice of the target image sequence by performing a hash operation based on the index information SeriesUID of the lead image slice until the obtained a hash value is the same as the index information hash(n) of the last image slice. Then, the processing device 140 may determine the index information of each image slice has been obtained.

In some embodiments, if the index information of the target image sequence includes the amount of the at least one image slice, when the count of the obtained hash values is one fewer than the count of the at least one image slice, the processing device 140 may determine the index information of each image slice has been obtained. For example, if index information of the target image sequence stored in the index table includes the index information SeriesUID of the lead image slice and the amount N of the at least one image slice, the processing device 140 may determine the index information of each image slice of the target image sequence by performing a hash operation based on the index information SeriesUID of the lead image slice until an amount of the obtained hash values equals (N−1). Then, the processing device 140 may determine the index information of each image slice has been obtained.

According to some embodiments of the present disclosure, the processing device 140 may determine the index information of the remaining image slices in the target image sequence based on the index information of the lead image slice, which may improve the efficiency and/or reliability of obtaining of index information of the at least one image slice in the target image sequence. In addition, the processing device 140 may determine whether the index information of each image slice has been obtained based on the index information of the last image slice or the amount of the at least one image slice, which may ensure accurate convergence in hash operation, thereby improving the stability of the index information of the at least one image slice of the target image sequence.

In 1830, the processing device 140 may obtain at least one image slice of the target image sequence based on the index information of each image slice of the target image sequence.

In some embodiments, the index information may further include storage IDs of a plurality of storage devices that store the at least one image slice. The processing device 140 may obtain the at least one image slice based on the index information of each image slice of the target image sequence. For example, the index information of each image slice may include an ID of the image slice or an ID of an image file of the image slice. On basis of the storage IDs of a plurality of storage devices, the processing device 140 may rapidly and accurately obtain, from the plurality of storage devices, each image slice based on the ID of the image slice or the ID of the image file of the image slice.

According to some embodiments of the present disclosure, the processing device 140 may obtain the index information of the target image sequence from the index table based on the series instance UID of the target image sequence. The index information of the target image sequence may include the index information of the lead image slice of the target image sequence. Then, the processing device 140 may determine the index information of the remaining image slices in the target image sequence based on the index information of the lead image slice. Further, the processing device 140 may obtain the at least one image slice of the target image sequence based on the index information of each image slice of the target image sequence. When the target image sequence needs to be obtained, after the index information of the lead image slice is obtained, the index information of the remaining image slices in the target image sequence may be obtained based on the index information of the lead image slice. Compared with a conventional storage method which involves querying the index information of each image slice one by one, the method of the present disclosure may improve the efficiency and/or reliability of obtaining the target image sequence, thereby improving the access performance of medical images.

Figure 19:
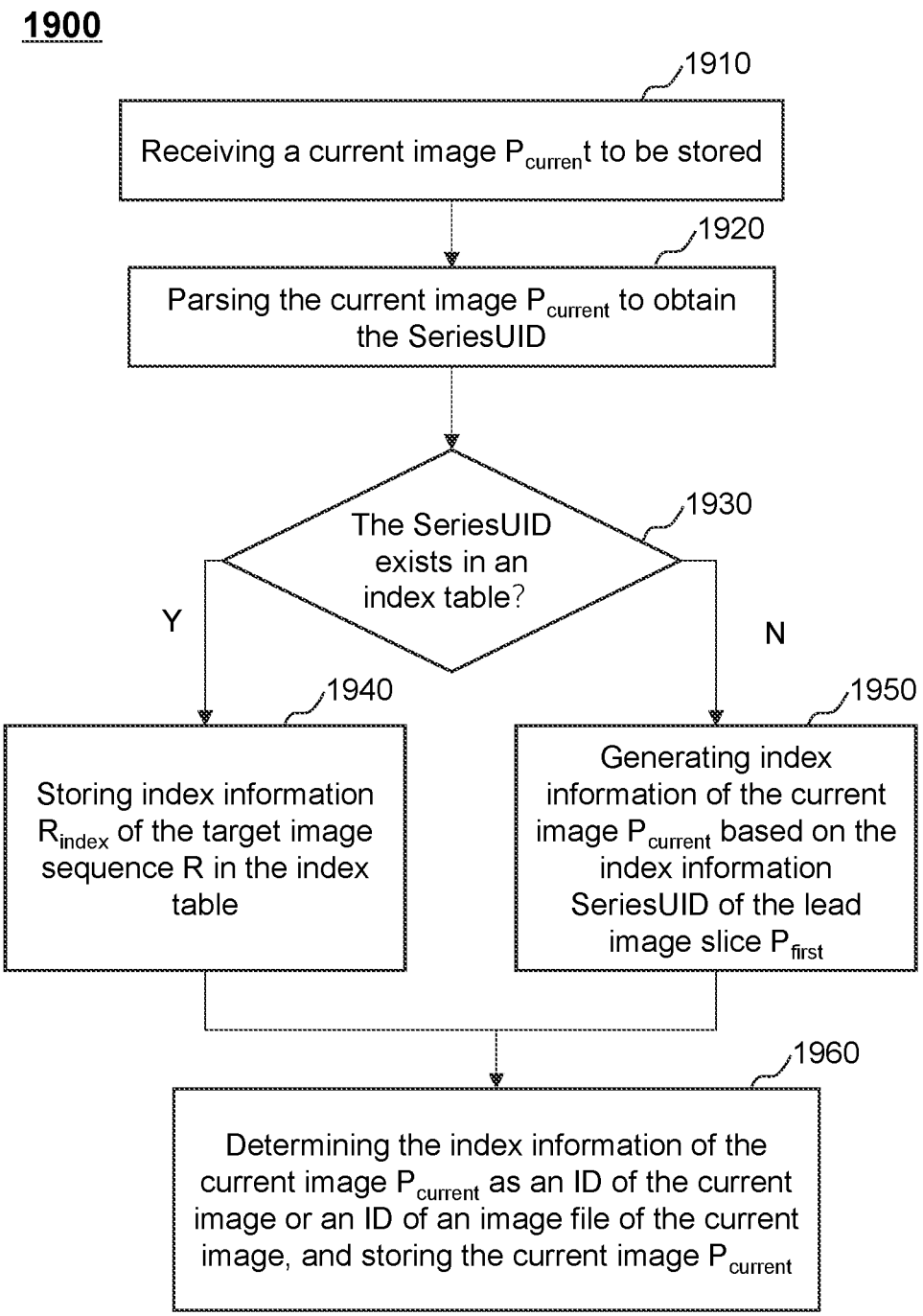
FIG. 19 is a flowchart illustrating an exemplary process for archiving an image sequence according to some embodiments of the present disclosure.

FIG. 19 is a flowchart illustrating an exemplary process 1900 for archiving an image sequence according to some embodiments of the present disclosure. In some embodiments, the process 1900 may be implemented in the imaging system 100 illustrated in FIG. 1. For example, the process 1900 may be stored in a storage (e.g., the storage device 150, the storage device 220, the storage 390) as a form of instructions, and invoked and/or executed by the processing device 140 (e.g., the processor 210 of the computing device 200 as illustrated in FIG. 2, the CPU 340 of the mobile device 300 as illustrated in FIG. 3, and/or one or more modules as illustrated in FIGS. 4-8). The operations of the illustrated process presented below are intended to be illustrative. In some embodiments, the process 1900 may be accomplished with one or more additional operations not described, and/or without one or more of the operations discussed. Additionally, the order in which the operations of the process 1900 as illustrated in FIG. 19 and described below is not intended to be limiting.

A target image sequence R may be taken as an example. The series instance UID of the target image sequence R may be represented as SeriesUID, and index information of a lead image slice $P_{first}$ of the target image sequence R is designated as SeriesUID.

In 1910, the processing device 140 may receive a current image $P_{current}$ to be stored. The current image P current may be any image slice in the target image sequence R.

In 1920, the processing device 140 may parse the current image $P_{current}$ to obtain the SeriesUID. Each image slice of the target image sequence R may be labelled with the SeriesUID. Therefore, the processing device 140 may obtain the SeriesUID by parsing the current image $P_{current}$.

In 1930, the processing device 140 may determine whether the SeriesUID exists in an index table. The index table may be configured to store index information of multiple image sequences that has been stored. In response to determining that the SeriesUID exists in the index table, it indicates that at least one image slice of the target image sequence R has been stored. The processing device 140 may perform operation 1950. In response to determining that the SeriesUID does not exist in the index table, it indicates that the target image sequence R is not stored, the current image $P_{current}$ is the lead image slice $P_{first}$ of the target image sequence R and the processing device 140 may perform operation 1940.

In 1940, the processing device 140 may store index information $R_{index}$ of the target image sequence R in the index table. The index information $R_{index}$ of the target image sequence R may include the SeriesUID. After the index information $R_{index}$ of the target image sequence R is stored in the index table, the processing device may perform operation 1960.

In 1950, the processing device 140 may generate index information of the current image $P_{current}$ based on the index information SeriesUID of the lead image slice $P_{first}$.

In some embodiments, the processing device 140 may generate the index information of the current image $P_{current}$ according to a preset algorithm. For example, the processing device 140 may determine the index information of the current image $P_{current}$ based on index information of an immediately preceding image slice of the current image $P_{current}$. For example, if the current image $P_{current}$ is the second image of the target image sequence R, the index information of the current image $P_{current}$ may be a hash value generated based on the SeriesUID. As another example, if the current image $P_{current}$ is the third image of the target image sequence R, the index information of the current image $P_{current}$ may be a hash value generated based on a hash value of the second image.

In 1960, the processing device 140 may determine the index information of the current image $P_{current}$ as an ID of the current image or an ID of an image file of the current image $P_{current}$, and store the current image $P_{current}$.

Figure 20:
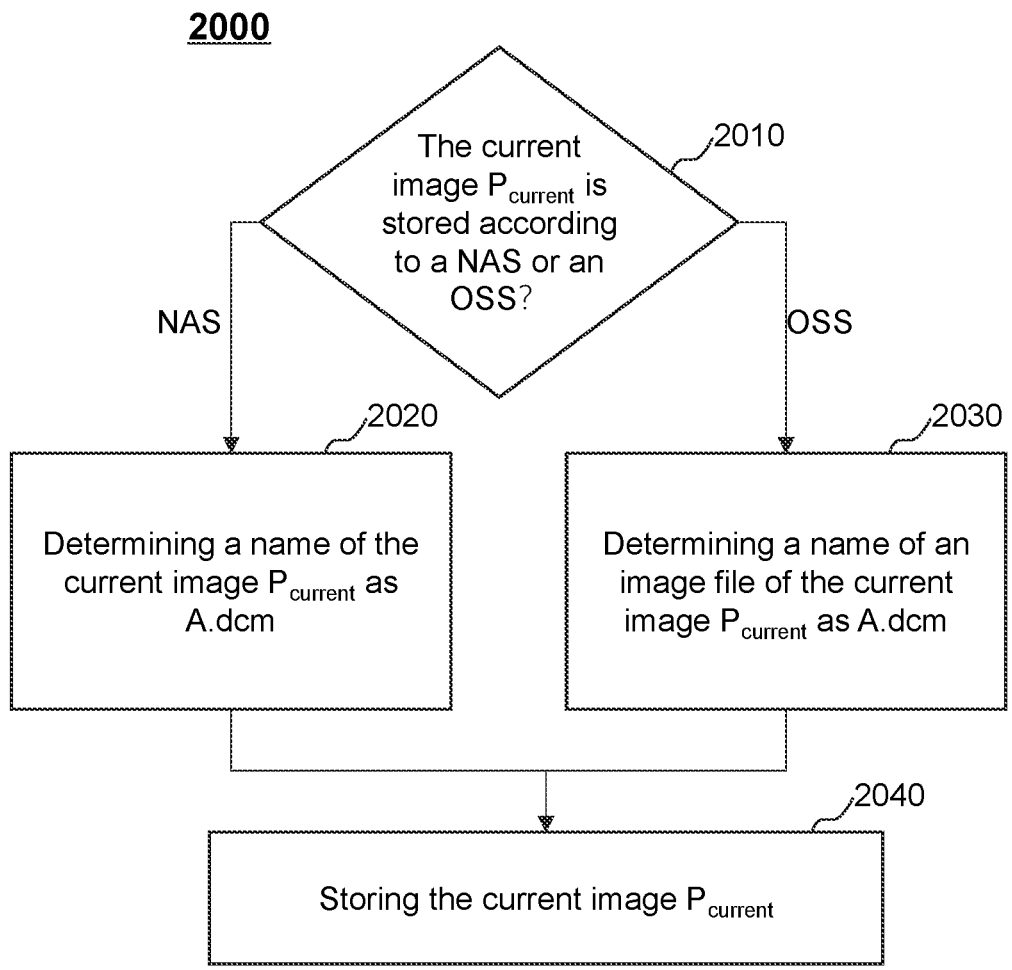
FIG. 20 is a flowchart illustrating an exemplary process for archiving an image according to some embodiments of the present disclosure.

FIG. 20 is a flowchart illustrating an exemplary process 2000 for archiving an image according to some embodiments of the present disclosure. One or more operations of the process 2000 may be performed to achieve at least part of operation 1960 as described in connection with FIG. 19.

Assuming that the index information of the current image $P_{current}$ is A, the process is 2000 may include operations 2010-2040. The series instance UID of the target image sequence R may be represented as SeriesUID, and index information of a lead image slice $P_{first}$ of the target image sequence R is SeriesUID.

In 2010, the processing device 140 may determine whether the current image $P_{current}$ is stored according to a NAS or an OSS.

In response to determining that the current image $P_{current}$ is stored according to the NAS, the processing device 140 may perform operation 2020. In response to determining that the current image $P_{current}$ is stored according to the OSS, the processing device 140 may perform operation 2030.

In 2020, the processing device 140 may determine a name of the current image $P_{current}$ as A·dcm. After the name of the current image $P_{current}$ is determined as A·dcm, the processing device may perform operation 2040.

In 2030, the processing device 140 may determine a name of an image file of the current image $P_{current}$ as A·dcm. After the name of an image file of the current image $P_{current}$ is determined as A·dcm, the processing device may perform operation 2040.

In 2040, the processing device 140 may store the current image $P_{current}$.

Figure 21:
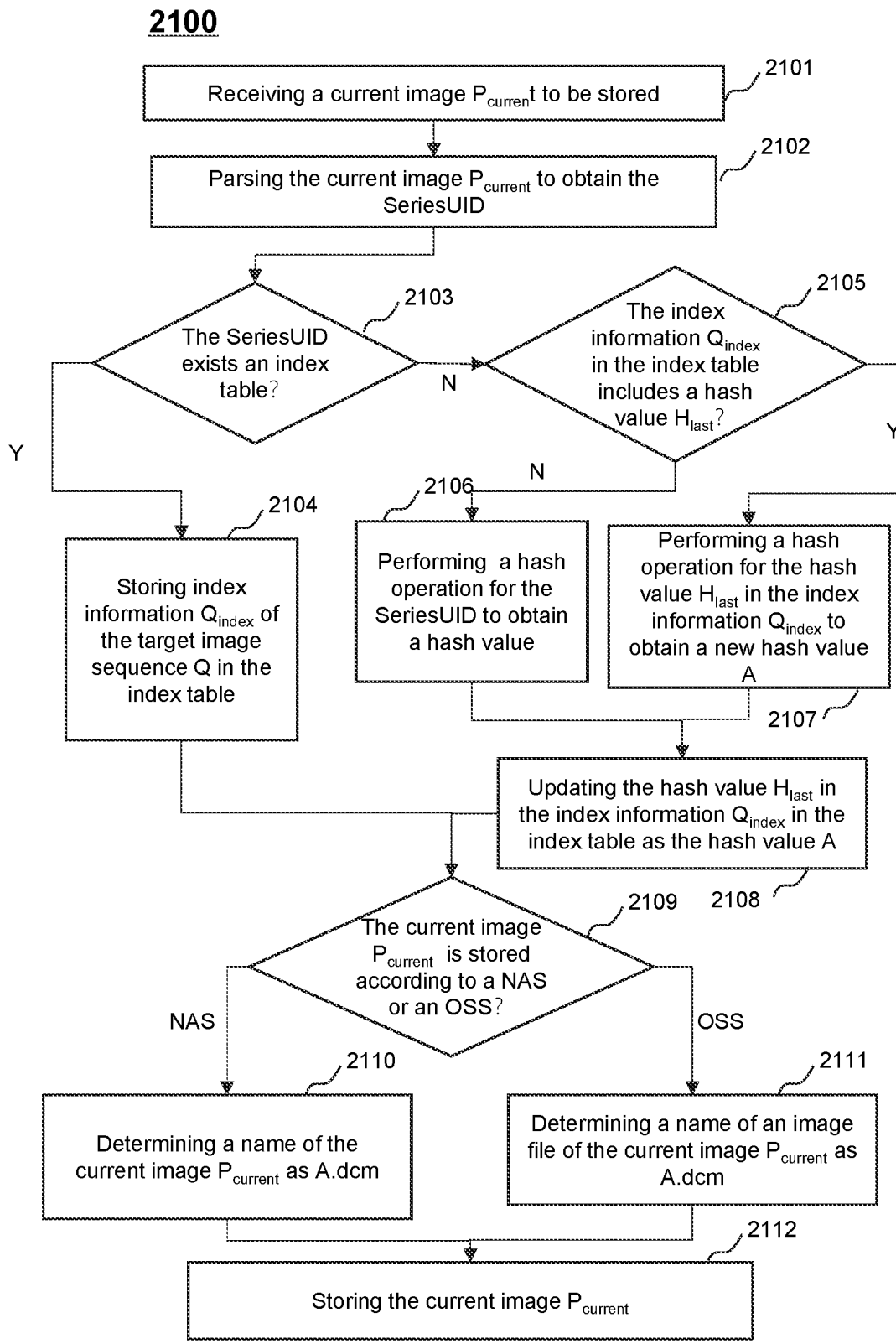
FIG. 21 is a flowchart illustrating an exemplary process for archiving an image sequence according to some embodiments of the present disclosure.

FIG. 21 is a flowchart illustrating an exemplary process 2100 for archiving an image sequence according to some embodiments of the present disclosure. In some embodiments, the process 2100 may be implemented in the imaging system 100 illustrated in FIG. 1. For example, the process 2100 may be stored in a storage (e.g., the storage device 150, the storage device 220, the storage 390) as a form of instructions, and invoked and/or executed by the processing device 140 (e.g., the processor 210 of the computing device 200 as illustrated in FIG. 2, the CPU 340 of the mobile device 300 as illustrated in FIG. 3, and/or one or more modules as illustrated in FIGS. 4-8). The operations of the illustrated process presented below are intended to be illustrative. In some embodiments, the process 2100 may be accomplished with one or more additional operations not described, and/or without one or more of the operations discussed. Additionally, the order in which the operations of the process 2100 as illustrated in FIG. 21 and described below is not intended to be limiting.

A target image sequence Q may be taken as an example. The series instance UID of the target image sequence Q may be represented as SeriesUID. Index information $Q_{index}$ of the target image sequence Q may include index information of a lead image slice $P_{first}$ of the target image sequence Q, storage IDs of a plurality of storage devices that store the target image sequence Q, and index information of a last image slice $P_{last}$ of the target image sequence that have been stored. The index information of the lead image slice $P_{first}$ may be the SeriesUID, and index information of the last image slice $P_{last}$ may be a hash value $H_{last}$.

The index information determining rule of the target image sequence Q may be that index information of each of the remaining image slices of the target image sequence Q is generated based on index information of an immediately preceding image slice which is immediately next to the image slice.

In 2101, the processing device 140 may receive a current image $P_{current}$ to be stored. The current image $P_{current}$ may be any image slice in the target image sequence Q.

In 2102, the processing device 140 may parse the current image $P_{current}$ to obtain the SeriesUID. Each image slice of the target image sequence Q may be labelled with the SeriesUID. Therefore, the processing device 140 may obtain the SeriesUID by parsing the current image $P_{current}$.

In 2103, the processing device 140 may determine whether the SeriesUID exists in an index table. The index table may be configured to store index information of multiple image sequences that has been stored. In response to determining that the SeriesUID exists in the index table, it indicates that at least one image slice of the target image sequence Q has been stored, and the processing device 140 may perform operation 2105. In response to determining that the SeriesUID does not exist in the index table, it indicates that the target image sequence Q is not stored, the current image $P_{current}$ is the lead image slice $P_{first}$ of the target image sequence Q, and the processing device 140 may perform operation 2104.

In 2104, the processing device 140 may store index information $Q_{index}$ of the target image sequence Q in the index table. The index information $Q_{index}$ of the target image sequence Q may include the SeriesUID and a storage ID of a storage device that stores the current image $P_{current}$. After the index information $Q_{index}$ of the target image sequence Q is stored in the index table the processing device may perform operation 2109.

In 2105, the processing device 140 may determine whether the index information $Q_{index}$ in the index table includes a hash value $H_{last}$.

The last image slice $P_{last}$ refers to a image slice of the target image sequence that was stored at last when the current image $P_{current}$ is obtained. For example, if five image slices of the target image sequence Q have been stored when the current image $P_{current}$ is obtained, the last image slice $P_{last}$ is the fifth image of the target image sequence Q, and the index information of the last image slice $P_{last}$ is the index information of the fifth image.

In response to determining that the index information $Q_{index}$ in the index table includes a hash value $H_{last}$, it indicates that at least two image slices of the target image sequence Q have been stored when the current image $P_{current}$ is obtained, and the current image $P_{current}$ is at least the third image of the target image sequence Q. In this case, the processing device 140 may perform operation 2107. In response to determining that the index information $Q_{index}$ in the index table does not include a hash value $H_{last}$, it indicates that only one image slice of the target image sequence Q has been stored when the current image $P_{current}$ is obtained, and the current image $P_{current}$ is the second image slice of the target image sequence Q. In this case, the processing device 140 may perform operation 2106.

In 2106, the processing device 140 may perform a hash operation for the SeriesUID to obtain a hash value.

When the current image $P_{current}$ is the second image of the target image sequence Q, the hash value obtained by performing a hash operation for the SeriesUID may be the index information of the current image $P_{current}$. After the index information of the current image $P_{current}$ is obtained, the processing device 140 may perform operation 2108.

In 2107, the processing device 140 may perform a hash operation for the hash value $H_{last}$ in the index information $Q_{index}$ to obtain a new hash value A.

When the current image $P_{current}$ is at least the third image of the target image sequence Q, the hash value $H_{last}$ in the index information $Q_{index}$ may be the index information of an immediately preceding image slice of the current image $P_{current}$. The hash value A obtained by performing a hash operation for the hash value $H_{last}$ may be the index information of the current image $P_{current}$. After the index information of the current image $P_{current}$ is obtained, the processing device 140 may perform operation 2108.

In 2108, the processing device 140 may update the hash value $H_{last}$ in the index information $Q_{index}$ in the index table as the hash value A.

After the current image $P_{current}$ is stored, the current image $P_{current}$ is the last image slice of the target image sequence. Therefore, the processing device 140 may update the hash value $H_{last}$ in the index information $Q_{index}$ in the index table as the hash value A.

In 2109, the processing device 140 may determine whether the current image $P_{current}$ is stored according to a NAS or an OSS. In response to determining that the current image $P_{current}$ is stored according to a NAS, the processing device 140 may perform operation 2110. In response to determining that the current image $P_{current}$ is stored according to an OSS, the processing device 140 may perform operation 2111.

In 2110, the processing device 140 may determine a name of the current image $P_{current}$ as A·dcm. After the name of the current image $P_{current}$ is determined as A·dcm, the processing device may perform operation 2112.

In 2111, the processing device 140 may determine a name of an image file of the current image $P_{current}$ as A·dcm. After the name of an image file of the current image $P_{current}$ is determined as A·dcm, the processing device may perform operation 2112.

In 2112, the processing device 140 may store the current image $P_{current}$.

In the process 2100, the index information $Q_{index}$ of the target image sequence Q may include index information of a lead image slice $P_{first}$ of the target image sequence Q, storage IDs of a plurality of storage devices that store the target image sequence Q, and index information of a last image slice $P_{last}$ of the target image sequence that have been stored. After the current image $P_{current}$ is stored, the processing device 140 may update the index information of the last image slice $P_{last}$ as the index information of the current image $P_{current}$. In this way, the index information of the at least one image slice of the target image sequence Q may be connected to form a hash chain according to a hash algorithm. In this way, an occupied storage space for storing the index information of the target image sequence Q is reduced, thereby improving the storage performance of medical images.

Figure 22:
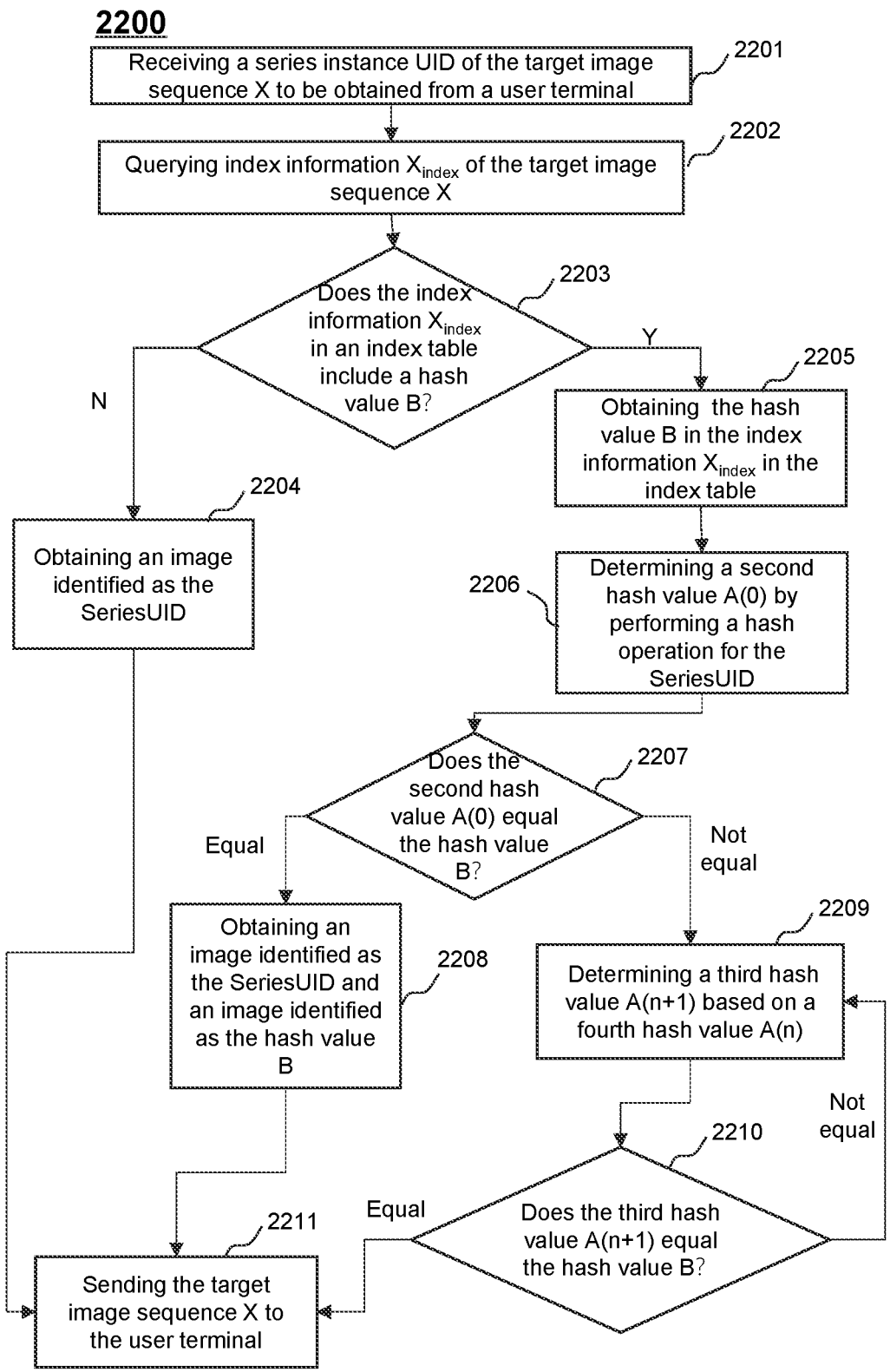
FIG. 22 is a flowchart illustrating an exemplary process for accessing an image sequence according to some embodiments of the present disclosure.

FIG. 22 is a flowchart illustrating an exemplary process 2200 for accessing an image sequence according to some embodiments of the present disclosure. In some embodiments, the process 2200 may be implemented in the imaging system 100 illustrated in FIG. 1. For example, the process 2200 may be stored in a storage (e.g., the storage device 150, the storage device 220, the storage 390) as a form of instructions, and invoked and/or executed by the processing device 140 (e.g., the processor 210 of the computing device 200 as illustrated in FIG. 2, the CPU 340 of the mobile device 300 as illustrated in FIG. 3, and/or one or more modules as illustrated in FIGS. 4-8). The operations of the illustrated process presented below are intended to be illustrative. In some embodiments, the process 2200 may be accomplished with one or more additional operations not described, and/or without one or more of the operations discussed. Additionally, the order in which the operations of the process 2200 as illustrated in FIG. 22 and described below is not intended to be limiting.

In 2201, the processing device 140 may receive a series instance UID of the target image sequence X to be obtained from a user terminal. The series instance UID of the target image sequence X may be represented as SeriesUID.

In 2202, the processing device 140 may query index information $X_{index}$ of the target image sequence X. The index information $X_{index}$ of the target image sequence X may include the SeriesUID and storage IDs of a plurality of storage devices that store at least one image slice of the target image sequence X. The index information of a lead image slice $P_{first}$ of the target image sequence X may be SeriesUID.

In 2203, the processing device 140 may determine whether the index information $X_{index}$ in an index table includes a hash value B.

The hash value B may correspond index information of a last image slice of the target image sequence X. The last image slice of the target image sequence X refers to a image slice of the target image sequence X that is stored at last (or obtained last during an examination).

The index table may be configured to store index information of multiple image sequences that has been stored. In response to determining that the index information $X_{index}$ in the index table includes a hash value, it indicates that the target image sequence X includes at least two stored image slices. In this case, the processing device 140 may perform operation 2205. In response to determining that the index information $X_{index}$ in the index table does not include any hash value, it indicates that the target image sequence X includes only one stored image slice. In this case, the processing device 140 may perform operation 2204.

In 2104, the processing device 140 may obtain an image identified as the SeriesUID.

When the index information $X_{index}$ in the index table does not include any hash value, it indicates that the target image sequence X includes only one stored image slice (i.e., the lead image slice $P_{first}$). The index information of a lead image slice $P_{first}$ is the SeriesUID. Therefore, the processing device 140 may obtain the lead image slice $P_{first}$ based on the storage ID of the storage device that stores the lead image slice $P_{first}$ and the SeriesUID.

In some embodiments, the processing device 140 may obtain the image identified as the SeriesUID to a buffer memory. After the lead image slice $P_{first}$ is obtained, the processing device may perform operation 2211.

In 2205, the processing device 140 may obtain the hash value B in the index information $X_{index}$ in the index table.

In 2206, the processing device 140 may determine a second hash value A(0) by performing a hash operation on the SeriesUID. The second hash value A(0) may be the index information of the second image of the target image sequence X.

In 2207, the processing device 140 may determine whether the second hash value A(0) equals the hash value B.

In response to determining that the second hash value A(0) equals the hash value B, it indicates that the target image sequence X include two image slices. In this case, the processing device 140 may perform operation 2208. In response to determining that the second hash value A(0) does not equal the hash value B, it indicates that the target image sequence X include at least three image slices. In this case, the processing device 140 may perform operation 2209.

In 2208, the processing device 140 may obtain an image identified as the SeriesUID and an image identified as the hash value B.

In some embodiments, the processing device 140 may obtain the image identified as the SeriesUID and the image identified as the hash value B to a buffer memory. When the target image sequence X include two image slices, the index information of the lead image slice $P_{first}$ is the SeriesUID, and the index information of the other image slice (i.e., the last image slice) is the hash value B. Therefore, the processing device 140 may obtain the lead image slice $P_{first}$ and the last image slice based on the storage IDs of the plurality of storage devices, the SeriesUID, and hash value B. After the image identified as the SeriesUID and the image identified as the hash value B are obtained, the processing device may perform operation 2211.

In 2209, the processing device 140 may determine a third hash value A(n+1) based on a fourth hash value A(n), wherein n is an integer equal to or greater than 0. The processing device 140 may perform a hash operation on the fourth hash value A(n) to determine the third hash value A(n+1).

In 2210, the processing device 140 may determine whether the third hash value A(n+1) equals the hash value B.

In response to determining that the third hash value A(n+1) equals the hash value B, the processing device 140 may obtain an image identified as the SeriesUID, an image identified as the hash value B, and an image identified as each of A(0)-A(n), and then the processing device may perform operation 2211. In response to determining that the third hash value A(n+1) does not equal the hash value B, the processing device 140 may increase n and repeat the operation 2209.

In 2211, the processing device 140 may send the target image sequence X to the user terminal.

In the process 2200, the processing device 140 determines the index information of the image slice of the target image sequence based on index information of an immediately preceding image slice of an image slice according to a hash algorithm. The processing device 140 may perform a hash operation for the index information of the lead image slice to obtain a hash value of the lead image slice, and designate the hash value of the lead image slice as the index information of the second image slice. The processing device 140 may perform a hash operation for the index information of the second image slice to obtain a hash value of the second image slice, and designate the hash value of the second image slice as the index information of the third image slice. The obtaining of the index information of each of the remaining image slices may be performed in a similar manner as that of the index information of the second image slice or the third image slice until the obtained hash value equals the index information of the last image slice. In this way, the processing device 140 may obtain the index information of each image slice of the target image sequence X. The processing device 140 may further obtain at least one image slice of the target image sequence X based on the index information of each image slice of the target image sequence X, which may greatly improve the efficiency and/or reliability of the obtaining of the target image sequence X.

It will be apparent to those skilled in the art that various changes and modifications can be made in the present disclosure without departing from the spirit and scope of the disclosure. In this manner, the present disclosure may be intended to include such modifications and variations if the modifications and variations of the present disclosure are within the scope of the appended claims and the equivalents thereof.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate a certain variation (e.g., ±1%, ±5%, ±10%, or ±20%) of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable. In some embodiments, a classification condition used in classification or determination is provided for illustration purposes and modified according to different situations. For example, a classification condition that "a value is greater than the threshold value" may further include or exclude a condition that "the probability value is equal to the threshold value."

What is claimed is:

1. A system for medical image data storage, comprising:
   a medical imaging device;
   at least one storage device including a set of instructions; and
   at least one processor in communication with the at least one storage device, wherein when executing the set of instructions, the at least one processor is directed to cause the system to perform operations including:
   generating, by the image device, a medical image file, wherein the medical image file includes a plurality of image slices;
   storing, by the at least one processor, onto a first storage device, metadata of the medical image file, wherein the metadata of the medical image file includes index information of the plurality of image slices, wherein the index information of the plurality of image slices is determined by:
identifying, by the at least one processor, a series instance unique identifier (UID) of the plurality of image slices; and
determining, by the at least one processor, the index information of the plurality of image slices based on the series instance UID, wherein the index information includes a hash value for each of the plurality of image slices, wherein the determining, by the at least one processor, the index information of the plurality of image slices based on the series instance UID includes:
determining a hash value of a first image slice which is immediately next to a second image slice of the plurality of image slices based on a hash value of the second image slice;
generating, by the at least one processor, at least one sub-image data set based on image data of the medical image file;
storing, by the at least one processor, onto a second storage device of at least one second storage device, each sub-image data set of the at least one sub-image data set, wherein the first storage device is different from each of the at least one second storage device; and
storing, by the at least one processor, onto the first storage device, access information of the at least one second storage device.

2. The system of claim 1, wherein the storing, onto the first storage device, the metadata of the medical image file includes:
obtaining, by the at least one processor, encrypted metadata by encrypting the metadata of the medical image file; and
storing, by the at least one processor, onto the first storage device, the encrypted metadata.

3. The system of claim 1, wherein the dividing the image data of the medical image file into at least one sub-image data set includes:
obtaining, by the at least one processor, compressed image data by compressing the image data of the medical image file; and
dividing, by the at least one processor, the compressed image data into the at least one sub-image data.

4. The system of claim 3, wherein the operations further include:
obtaining, by the at least one processor, at least one encoded sub-image data set by encoding the at least one sub-image data set; and
the storing, by the at least one processor, onto a second storage device of the at least one second storage device, each sub-image data set of the at least one sub-image data set includes:
storing, by the at least one processor, onto a second storage device of the at least one second storage device, each encoded sub-image data set of the at least one encoded sub-image data set.

5. The system of claim 1, wherein the operations further include:
obtaining, by the at least one processor, access information of the at least one second storage device; and
generating, by the at least one processor, the metadata of the medical image file based on the access information of the image data.

6. The system of claim 1, wherein the operations further include:
modifying or deleting, by the at least one processor, the at least a portion of the medical image file; and
updating, by the at least one processor, the metadata of the medical image file.

7. A system for accessing medical image data, comprising:
at least one storage device including a set of instructions; and
at least one processor in communication with the at least one storage device, wherein when executing the set of instructions, the at least one processor is directed to cause the system to perform operations including:
obtaining, by the at least one processor, from a user terminal, a request for accessing a medical image file, wherein the medical image file includes a plurality of image slices, and the medical image file is generated from a medical imaging device;
obtaining, by the at least one processor, from a first storage device, metadata of the medical image file based on the request, wherein the metadata of the medical image file includes index information of the plurality of image slices, wherein the index information of the plurality of image slices is determined by:
identifying, by the at least one processor, a series instance unique identifier (UID) of the plurality of image slices; and
determining, by the at least one processor, the index information of the plurality of image slices based on the series instance UID, wherein the index information includes a hash value for each of the plurality of image slices, wherein the determining, by the at least one processor, the index information of the plurality of image slices based on the series instance UID includes:
determining a hash value of a first image slice which is immediately next to a second image slice of the plurality of image slices based on a hash value of the second image slice;
obtaining, by the at least one processor, from the first storage device, access information of at least one second storage device that stores image data of the medical image file based on the metadata, wherein the first storage device is different from each of the at least one second storage device;
obtaining, by the at least one processor, from the at least one second storage device, at least one sub-image data set of the image data; and
obtaining, by the at least one processor, the medical image file by combining the metadata and the at least one sub-image data set.

8. The system of claim 7, wherein the request further includes modifying or deleting at least a portion of the medical image file, and the operations further include:
modifying or deleting, by the at least one processor, the at least a portion of the obtained medical image file based on the request; and
updating, by the at least one processor, at least a portion of the metadata of the medical image file.

9. The system of claim 7, wherein the metadata of the medical image file is encrypted, and the obtaining, from the first storage device, the metadata of the medical image file based on the request includes:

obtaining, by the at least one processor, decrypted metadata by decrypting the metadata obtained from the first storage device.

10. The system of claim 9, wherein the obtaining the medical image file by combining the metadata and the at least one sub-image data set includes:
   obtaining, by the at least one processor, compressed image data by combining the at least one sub-image data set;
   obtaining, by the at least one processor, decompressed image data by decompressing the compressed image data; and
   obtaining, by the at least one processor, the medical image file by combining the decompressed image data and the decrypted metadata.

11. A system for medical image data storage, comprising:
   at least one storage device including a set of instructions; and
   at least one processor in communication with the at least one storage device, wherein when executing the set of instructions, the at least one processor is directed to cause the system to perform operations including:
      obtaining, by accessing the at least one storage device by the at least one processor, a plurality of medical image slices, wherein the plurality of medical image slices are generated from a medical imaging device;
      identifying, by the at least one processor, a series instance unique identifier (UID) of the plurality of medical image slices;
      determining, by the at least one processor, index information of the plurality of medical image slices based on the series instance UID, wherein the index information includes the series instance UID, and the index information includes a hash value for each of the plurality of medical image slices, wherein the determining, by the at least one processor, the index information of the plurality of medical image slices based on the series instance UID includes:
         determining a hash value of a first medical image slice which is immediately next to a second medical image slice of the plurality of medical image slices based on a hash value of the second medical image slice; and
      storing, by the at least one processor, the plurality of medical image slices based on the index information of the plurality of medical image slices.

12. The system of claim 11, wherein the index information further includes a hash value of a last medical image of the plurality of medical image slices.

13. The system of claim 12, wherein the determining, by the at least one processor, the index information of the plurality of medical image slices based on the series instance unique identifier UID includes:
   for the each medical image slice of the plurality of medical image slices, determining, by the at least one processor, the hash value according to a hash algorithm.

14. The system of claim 13, wherein a hash value of a lead medical image slice of the plurality of medical image slices is designated as the series instance UID.

15. The system of claim 14, wherein the index information further includes a storage ID of a storage device that stores the lead medical image slice.

16. The system of claim 15, wherein the plurality of medical image slices are stored according to a network attached storage (NAS), and the hash value for each medical image slice of the plurality of medical image slices is designated as an ID of the medical image slice.

17. The system of claim 15, wherein the plurality of medical image slices are stored according to an object storage service (OSS), and the hash value for each medical image slice of the plurality of medical image slices is designated as an ID of an image file of the medical image slice.

* * * * *